(12) United States Patent
Flores et al.

(10) Patent No.: US 7,786,287 B2
(45) Date of Patent: Aug. 31, 2010

(54) HEPATITIS C VIRUS ASSAY SYSTEMS

(75) Inventors: Osvaldo A. Flores, North Wales, PA (US); Jay Grobler, Gwynedd, PA (US); Edward M. Murray, Limerick, PA (US); Paul D. Zuck, Trenton, NJ (US)

(73) Assignee: Merck & Co., Inc., Rahway, NJ (US)

( * ) Notice: Subject to any disclaimer, the term of this patent is extended or adjusted under 35 U.S.C. 154(b) by 575 days.

(21) Appl. No.: 10/510,912

(22) PCT Filed: Apr. 11, 2003

(86) PCT No.: PCT/US03/12509

§ 371 (c)(1),
(2), (4) Date: Oct. 8, 2004

(87) PCT Pub. No.: WO03/089672

PCT Pub. Date: Oct. 30, 2003

(65) Prior Publication Data

US 2005/0181356 A1    Aug. 18, 2005

Related U.S. Application Data

(60) Provisional application No. 60/372,847, filed on Apr. 16, 2002.

(51) Int. Cl.
| | |
|---|---|
| *C07H 21/00* | (2006.01) |
| *C12P 21/00* | (2006.01) |
| *C12N 15/00* | (2006.01) |
| *C12N 15/51* | (2006.01) |
| *C12N 7/00* | (2006.01) |

(52) U.S. Cl. ............ 536/23.72; 435/69.1; 435/235.1; 435/320.1

(58) Field of Classification Search .............. None
See application file for complete search history.

(56) References Cited

U.S. PATENT DOCUMENTS

| | | | |
|---|---|---|---|
| 5,739,002 A | | 4/1998 | De Francesco et al. |
| 5,741,657 A | | 4/1998 | Tsien et al. |
| 5,783,669 A | * | 7/1998 | Hawkins et al. ............ 530/350 |
| 5,885,779 A | | 3/1999 | Sadowksi et al. |
| 6,063,562 A | * | 5/2000 | Melnick et al. ............... 435/5 |
| 6,297,003 B1 | * | 10/2001 | Rice et al. ..................... 435/5 |
| 6,630,343 B1 | | 10/2003 | Bartenschlager |
| 2002/0142350 A1 | | 10/2002 | Kukolj et al. |
| 2004/0018529 A1 | * | 1/2004 | Li et al. ........................ 435/6 |

FOREIGN PATENT DOCUMENTS

| | | | |
|---|---|---|---|
| DE | 199 15 178 | | 5/2000 |
| EP | 1 043 399 A2 | | 10/2000 |
| WO | WO 96/37619 | | 11/1996 |
| WO | WO 01/89364 | * | 11/2001 |
| WO | WO 02/059321 | * | 8/2002 |

OTHER PUBLICATIONS

Alter, H. "To C or Not To C: These Are the Questions", Blood, 1995, vol. 85, pp. 1681-1695.
Ambler, R. "The structure of β-lactamases", Phil. Trans. R. Soc. Lond. B. Biol. Sci., 1980, vol. 289, pp. 321-331.
Bartenschlager, R. et al. "Nonstructural Protein 3 of the Hepatitis C Virus Encodes a Serine-Type Proteinase Required for Cleavage at the NS3/4 and NS4/5 Junctions", Journal of Virology, 1993, vol. 67, pp. 3835-3844.
Behrens, S. et al. "Identification and properties of the RNA-dependent RNA polymerase of hepatitis C virus", The EMBO Journal, 1996, vol. 15, pp. 12-22.
Blight, K. et al. "Efficient Initiation of HCV RNA Replication in Cell Culture", Science, 2000, vol. 290, pp. 1972-1974.
Castelain, S. et al. "Variability of the Nonstructural 5A Protein of Hepatitis C Virus Type 3a Isolates and Relation to Interferon Sensitivity", The Journal of Infectious Diseases, 2002, vol. 185, pp. 573-583.
Chamberlain, R. et al. "Complete nucleotide sequence of a type 4 hepatitis C virus variant, the predominant genotype in the Middle East", Journal of General Virology, 1997, vol. 78, pp. 1341-1347.
Choo, Q. et al. "Isolation of a cDNA Clone Derived from a Blood-Borne Non-A, Non-B Viral Hepatitis Genome", Science, 1989, vol. 244, pp. 359-262.
De Francesco, R. et al. "Biochemical and Immunologic Properties of the Nonstructural Proteins of the Hepatitis C Virus: Implications for Development of Antiviral Agents and Vaccines", Seminars in Liver Disease, 2000, vol. 20, pp. 69-83.
Failla, C. et al. "Both NS3 and NS4A Are Required for Proteolytic Processing of Hepatitis C Virus Nonstructural Proteins", Journal of Virology, 1994, vol. 68, pp. 3753-3760.
Farci, P. et al. "Early changes in hepatitis C viral quasispecies during interferon therapy predict the therapeutic outcome", Proc. Natl. Acad. Sci. USA, 2002, vol. 99, pp. 3081-3086.
Grahovac, B. et al. "Dynamics of serum hepatitis C virus load and quasispecies complexity during antiviral therapy in patients with chronic hepatitis C", Journal of Clinical Virology, 2001, vol. 20, pp. 85-89.
Grakoui, A. et al. "A second hepatitis C virus-encoded proteinase", Proc. Natl. Acad. Sci. USA, 1993, vol. 90, pp. 10583-10587.
Grakoui, A. et al. "Expression and Identification of Hepatitis C Virus Polyprotein Cleavage Products", Journal of Virology, 1993, vol. 67, pp. 1385-1395.
Hijikata, M. et al. "Proteolytic processing and membrane association of putative nonstructural proteins of hepatitis C virus", Proc. Natl. Acad. Sci. USA, 1993, vol. 90, pp. 10773-10777.

(Continued)

*Primary Examiner*—Zachariah Lucas
(74) *Attorney, Agent, or Firm*—Melissa B. Wenk

(57) ABSTRACT

The present invention features assays employing a beta-lactamase reporter system, an HCV replicon enhanced cell, and/or a chimeric HCV replicon containing a 3' UTR based on the HCV-1a 3' UTR. These features can be employed alone or together, and are preferably combined together to measure HCV replicon activity and the affect of compounds on such activity.

5 Claims, 12 Drawing Sheets

OTHER PUBLICATIONS

Honda, M. et al. "Structural Requirements for Initiation of Translation by Internal Ribosome Entry within Genome-Length Hepatitis C Virus RNA", Virology, 1996, vol. 222, pp. 31-42.

Iwarson, S. "The natural course of chronic hepatitis C", FEMS Microbiology Reviews, 1994, vol. 14, pp. 201-204.

Kadonaga, J. et al. "The Role of the β-Lactamase Signal Sequence in the Secretion of Proteins by *Escherichia coli*", The Journal of Biological Chemistry, 1984, vol. 259, pp. 2149-2154.

Kew, M. "Hepatitis C virus and hepatocellular carcinoma", FEMS Microbiology Reviews, 1994, vol. 14, pp. 211-219.

Kolykhalov, A. et al. "Hepatitis C Virus-Encoded Enzymatic Activities and Conserved RNA Elements in the 3' Nontranslated Region Are Essential for Virus Replication In Vivo", Journal of Virology, 2000, vol. 74, pp. 2046-2051.

Kolykhalov, A. et al. "Identification of a Highly Conserved Sequence Element at the 3' Terminus of Hepatitis C Virus Genome RNA", Journal of Virology, 1996, vol. 70, pp. 3363-3371.

Kuo, G. et al. "An Assay for Circulating Antibodies to a Major Etiologic Virus of Human Non-A, Non-B Hepatitis", Science, 1989, vol. 244, pp. 362-364.

Lohmann, V. et al. "Biochemical and Kinetic Analyses of NS5B RNA-Dependent RNA Polymerase of the Hepatitis C Virus", Virology, 1998, vol. 249, pp. 108-118.

Lohmann, V. et al. "Mutations in Hepatitis C Virus RNAs Conferring Cell Culture Adaptation", Journal of Virology, 2001, vol. 75, pp. 1437-1449.

Lohmann, V. et al. "Replication of Subgenomic Hepatitis C Virus RNAs in a Hepatoma Cell Line", Science, 1999, vol. 285, pp. 110-113.

Mizushima, H. et al. "Analysis of N-Terminal Processing of Hepatitis C Virus Nonstructural Protein 2", Journal of Virology, 1994, vol. 68, pp. 2731-2734.

Pawlotsky, J. "Hepatitis C virus (HCV) NS5A protein: role in HCV replication and resistance to interferon-α", Journal of Viral Hepatitis, 1999, vol. 6, Suppl. 1, pp. 47-48.

Pietschmann, T. et al. "Characterization of Cell Lines Carrying Self-Replicating Hepatitis C Virus RNAs", Journal of Virology, 2001, vol. 75, pp. 1252-1264.

Simmonds, P. "The origin and evolution of hepatitis viruses in humans", Journal of General Virology, 2001, vol. 82, pp. 693-712.

Takamizawa, A. et al. "Structure and Organization of the Hepatitis C Virus Genome Isloated from Human Carriers", Journal of Virology, 1991, vol. 65, pp. 1105-1113.

Tanaka, T. et al. "Structure of the 3' Terminus of the Hepatitis C Virus Genome", Journal of Virology, 1996, vol. 70, pp. 3307-3312.

Tomei, L. et al. "NS3 Is a Serine Protease Required for Processing of Hepatitis C Virus Polyprotein", Journal of Virology, 1993, vol. 67, pp. 4017-4026.

Wasley, A. et al. "Epidemiology of Hepatitis C: Geographic Differences and Temporal Trends", Seminars in Liver Disease, 2000, vol. 20, pp. 1-16.

Zlokarnik, G. "Fusions to β-Lactamase as a Receptor for Gene Expression in Live Mammalina Cells", Methods in Enzymology, 2000, vol. 321, pp. 221-244.

Zlokarnik, G. et al. "Quantitation of Transcription and Clonal Selection of Single Living Cells with b-Lactamase as Reporter", Science, 1998, vol. 279, pp. 84-88.

Bartenschlager, R. et al. "Replication of hepatitis C virus", Journal of General Virology, 2000, vol. 81, pp. 1631-1648.

Graziani, R. et al. "Dominant negative effect of wild-type NS5A on NS5A-adapted subgenomic hepatitis c virus RNA replicon", Journal of General Virology, 2004, vol. 85, pp. 1867-1875.

Ikeda, M. et al. "Selectable Subgenomic and Genome-Length Dicistronic RNA Derived from an Infectious Molecular Clone of the HCV-N Strain of Hepatitis C Virus Replicate Efficiently in Cultured Huh7 Cells", Journal of Virology, 2002, vol. 76, pp. 2997-3006.

Krieger, N. et al. "Enhancement of Hepatitis C Virus RNA Replication by Cell Culture-Adaptive Mutations", Journal of Virology, 2001, vol. 75, pp. 4614-4624.

Murray, E. et al. "Persistent Replication of Hepatitis C Virus Replicons Expressing the β-Lactamase Reporter in Subpopulations of Highly Permissive Huh7 Cells", Journal of Virology, 2003, vol. 77, pp. 2928-2935.

Zuck, P. et al. "A cell-based β-lactamase reporter gene assy for the identification of inhibitors of hepatitis C virus replication", Analytical Biochemistry, 2004, vol. 334, pp. 344-355.

* cited by examiner

```
   1 gccagccccc gauuggggc gacacuccac cauagaucac uccccuguga ggaacuacug
  61 ucuucacgca gaaagcgucu agccauggcg uuaguaugag ugucgugcag ccuccaggac
 121 cccccucccc gggagagcca uaguggucug cggaaccggu gaguacaccg gaauugccag
 181 gacgaccggg uccuucuug gaucaacccg cucaaugccu ggagauuugg gcgugccccc
 241 gcgagacugc uagccgagua guguugdguc gcgaaaggcc uguguguacu gccugauagg
 301 gugcuugcga gugccccggg aggucucgua gaccgugcac caugagcacg aauccuaaac
 361 cucaaagaaa aaccaaaggg cgcgccaugc acccagaaac gcuggugaaa guaaaagaug
 421 cugaagauca guugggugca cgagggguu acaucgaacu ggaucucaac agcgguaaga
 481 uccuugagag uuuucgcccc gaagaacguu uuccaaugau gagcacuuuu aaaguucugc
 541 uaugugcgc gguauuaucc cguauugacg ccgggcaaga gcaacucggu cgccgcauac
 601 acuauucuca gaaugacuug guugaguacu caccagucac agaaaagcau cuuacggaug
 661 gcaugacagu aagagaauua ugcagugcug ccauaaccau gagugauaac acugcggcca
 721 acuuacuucu gacaacgauc ggaggaccga aggagcuaac cgcuuuuug cacaacaugg
 781 gggaucaugu aacucgccuu gaucguuggg aaccggagcu gaaugaagcc auaccaaacg
 841 acgagcguga caccacgaug ccuguagcaa uggcaacaac guucgcaaa cuauuaacug
 901 gcgaacuacu uacucuagcu ucccggcaac aauuaauaga cuggauggag gcggauaaag
 961 uugcaggacc acuucugcgc ucggcccuuc cggcuggcug guuuauugcu gauaaaucug
1021 gagccgguga gcguggucu cgcgguauca uugcagcacu ggggccagau gguaagcccu
1081 cccguaucgu aguuaucuac acgacgggga gucaggcaac uaggaugaa cgaaauagac
1141 agaucgcuga gauaggugcc ucacugauua agcauggua aguuaaaca gaccacaacg
1201 guuucccucu agcgggauca auuccgcccc ucuccuccc cccccuaa cguuacuggc
1261 cgaagccgcu ggaauaagg ccggugugcg uuugucuaua guuauuuuc caccauauug
1321 ccgucuuuug gcaaugugag ggcccggaaa ccuggcccug ucuucuugac gagcauuccu
1381 aggggucuuu ccccucucgc caaaggaaug caaggucugu ugaaugucgu gaaggaagca
1441 guuccucugg aagcuucuug aagacaaaca acgucuguag cgacccuuug caggcagcgg
1501 aacccccac cuggcgacag gugccucugc ggccaaaagc cacguguaua agauacaccu
1561 gcaaaggcgg cacaacccca gugccacguu gugaguugga uaguugugga aagagucaaa
1621 uggcucuccu caagcguauu caacaagggg cugaaggaug cccagaaggu accccauugu
1681 augggaucug aucuggggcc ucggugcaca ugcuuuacau guguuagcu gagguuaaaa
1741 aacgucuagg ccccccgaac cacggggacg ugguuuccu uugaaaaaca cgauaauacc
1801 auggaccggg agauggcagc aucgugcgga ggcgcgguuu ucguaggucu gauacucuug
1861 accugucac cgcacauaa gcuguccuc gcuaggcuca uaugguguu acaauauuuu
1921 aucaccaggg ccgaggcaca cuugcaagug uggauccccc ccucaacgu ucgggggggc
1981 cgcgaugccg ucauccuccu cacgugcgcg auccacccag agcuaaucuu uaccaucacc
2041 aaaaucuugc ucgccauacu cgguccacuc auggugcucc aggcgguau aaccaaagug
2101 ccguacuucg ugcgcgcaca cgggcucauu cgugcaugca ugcuggugcg gaagguugcu
2161 gggggucauu augccaaau ggcucucaug aaguuggccg cacugacagg uacgacguu
2221 uaugaccauc ucacccccacu gcgggacugg gcccacgcgg ccuacgaga ccuugcgguq
2281 gcaguugagc ccgucgucuu cucugauaug gagaccaagg uuauaccug gggggcagac
2341 accgcggcgu gugggacau caucuugggc cugcccgucu ccgcccgcag ggggagggag
2401 auacaucugg gaccggcaga cagccuugaa gggcaggggu ggcgacuccu cgcgccuauu
2461 acggccuacu cccaacagac gcgaggccua cuuggcugca ucaucacuag ccucacaggc
```

FIG. 1A

```
2521 cgggacagga accaggucga gggggagguc caagugggucu ccaccgcaac acaaucuuuc
2581 cuggcgaccu gcgucaaugg cgugguguugg acugucuauc auggugccgg cucaaagacc
2641 cuugccggcc caaagggccc aaucacccaa auguacacca augugggacca ggaccucguc
2701 ggcuggcaag cgcccccgg ggcgcguucc uugacaccau gcaccgcgg cagcucggac
2761 cuuuacuugg ucacgaggca ugccgaugguc auccggugc gccggcgggg cgacagcagg
2821 gggagccuac ucuccccag gccgucucc uacuugaagg gcucucgggg cgguccacug
2881 cucugcccu cggggcacgc ugggggcauc uuucgggcug ccgugugcac ccgagggguu
2941 gcgaaggcgg uggacuuugu acccgucgag ucuauggaaa ccacuaugcg guccccgguc
3001 uucacggaca acucguccc ucggccgua ccgcagacau ccaggugggc ccaucuacac
3061 gccccuacug guagcggcaa gagcacuaag gugccggcug cguaugcagc ccaaggguau
3121 aaggugcuug uccugaaccc guccgucgcc gccacccuag guuucggggc guauaugucu
3181 aaggcacaug guaucgaccc uaacaucaga accggggguaa ggaccaucac cacgggugcc
3241 cccaucacgu acuccaccua uggcaaguuu cuugccgacg gugguugcuc uggggggcgcc
3301 uaugacauca uaauaugguga ugagugccac ucaacugacu cgaccacuau ccugggcauc
3361 ggcacagucc uggaccaagc ggagacggcu ggagcgcgac ucgucgugcu cgccaccgcu
3421 acgccuccgg gaucggucac cgugccacau ccaaacaucg aggagguggc ucuguccagc
3481 acuggagaaa ucccccuuuua uggcaaagcc auccccaucg agaccaucaa ggggggggagg
3541 caccucauuu ucugccauuc caagaagaaa uguggaugagc ucgccgcgaa gcugccggc
3601 cucggacuca augcuguagc auauuaccgg ggccuugaug uauccgucau accaacuagc
3661 ggagacguca uugucguagc aacggacgcu cuaaugacgg gcuuuaccgg cgauuucgac
3721 ucagugaucg acugcaauac augugucacc cagacagucg acuucagccu ggacccgacc
3781 uucaccauug agacgacgac cgugccacaa gacgcggugu cacgcucgca gcggcgaggc
3841 aggacugguua ggggcaggau gggcauuuac agguuuguga cuccaggaga acggcccucg
3901 ggcauguucg auccucggu ucugugcgag ugcuaugacg cgggcugugc uugguacgag
3961 cucacgcccg ccgagaccuc aguuagguug cgggcuuacc uaaacacacc agggugcccc
4021 gucugccagg accaucugga guucugggag agcgucuuua caggccucac ccacauagac
4081 gcccauuucu ugucccagac uaagcaggca ggagacaacu ucccuaccu gguagcauac
4141 caggcuacgg ugucgccag ggcucaggcu ccaccuccau cgugggacca aauguggaag
4201 ugucucauac ggcuaaagcc uacgcugcac gggccaacgc cccugcugua uaggcuggga
4261 gccguucaaa acgagguuac uaccacacac cccauaacca aauacaucau ggcaugcaug
4321 ucggcugacc uggagggucgu cacgagcacc uggggugcugg uaggcggagu ccuagcagcu
4381 cuggccgcgu auugccugac aacaggcagc guggucauug ugggcaggau caucuugucc
4441 ggaaagccgg ccaucauucc cgacagggaa guccuuuacc gggaguucga ugagauggaa
4501 gagugcgccu cacaccucc uuacaucgaa cagggaaugc agcucgccga acaauucaaa
4561 cagaaggcaa ucggguugcu gcaaacagcc accaagcaag cggaggcugc ugcucccgug
4621 guggaaucca agugggggac ccucgaagcc uucggggcga agcauaugug gaauuucauc
4681 agcgggauac aauauuuagc aggcuuugucc acucugccug gcaaccccgc gauagcauca
4741 cugauggcau ucacagccuc uaucaccagc ccgcucacca cccaacauac ccuccuguuu
4801 aacauccugg ggggaugggu ggccgcccaa cuugcccuc ccagcgcugc uucugcuuuc
4861 guaggcgccg gcaucgcugg agcggcuguu ggcagcauag gccuuggaa gggugcuugug
4921 gauauuuugg cagguuaugg agcagggggug gcaggcgcgc ucguggccuu uaaggucaug
4981 agcggcgaga ugccccucac cgaggaccug guuaaccuac ucccugcuau ccucucccu
```

FIG. 1B

```
5041 ggcgcccuag ucgucggggu cgugugcgca gcgauacugc gucggcacgu gggcccaggg
5101 gaggggcug ugcaguggau gaaccggcug auagcguucg cuucgcgggg uaaccacguc
5161 uccccacgc acuaugugcc ugagagcgac gcugcagcac gugucacuca gauccucucu
5221 agucuuacca ucacucagcu gcugaagagg cuucaccagu ggaucaacga ggacugcucc
5281 acgccaugcu ccggcucgug gcuaagagau guuugggauu ggauaugcac gguguugacu
5341 gauuucaaga ccuggcucca guccaagcuc cugccgcgau ugccgggagu ccccuucuuc
5401 ucaugucaac guggguacaa gggagucugg cggggcgacg gcaucaugca aaccaccugc
5461 ccauguggag cacagaucac cggacaugug aaaaacgguu ccaugaggau cgggggccu
5521 aggaccugua guaacacgug gcauggaaca uccccauua acgcguacac cacgggcccc
5581 ugcacgcccu ccccggcgcc aaauuauucu agggcgcugu ggcgggugc ugcugaggag
5641 uacguggagg uuacgcgggu ggggauuuc cacuacguga cgggcaugac cacugacaac
5701 guaaagugcc cgugucaggu uccggccccc gaauucuuca cagaagugga uggggugcgg
5761 uugcacaggu acgcuccagc gugcaaaccc cuccuacggg aggaggucac auuccugguc
5821 gggcucaauc aauaccuggu uggucacag cucccaugcg agcccgaacc ggacguagca
5881 gugcucacuu ccaugcucac cgaccccucc cacauuacgg cggagacggc uaagcguagg
5941 cuggccaggg gauccccccc cuccuuggcc agcucaucag cuauccagcu gucugcgccu
6001 uccuugaagg caacaugcac uaccgucau gacuccccgg acgcugaccu caucgaggcc
6061 aaccuccugu ggcggcagga gaugggcggg aacaucaccc gcguggaguc agaaaauaag
6121 guaguaauuu uggacucuuu cgagccgcuc caagcggagg aggaugagag ggaaguaucc
6181 guuccggcgg agauccugcg gagguccagg aaauucccuc gagcgaugcc cauaugggca
6241 cgcccggauu acaacccucc acuguuagag uccggaagg acccggacua cgucccucca
6301 gugguacacg ggugucauu gccgccugcc aaggcccuc cgauaccacc uccacggagg
6361 aagaggacgg uuguccuguc agaaucuacc gugucuucug ccuggcgga gcucgccaca
6421 aagaccuucg gcagcuccga aucgucggcc gucgacagcg gcacggcaac ggccucuccu
6481 gaccagcccu ccgacgacgg cgacgcggga uccgacguug agucguacuc cuccaugccc
6541 ccccuugagg gggagccggg ggaucccgau cucagcgacg ggucuugguc uaccguaagc
6601 gaggaggcua gugaggacgu cgucugcugc ucgauguccu acacauggac aggcgcccug
6661 aucacgccau gcgcugcgga ggaaaccaag cugcccauca augcacgag caacucuuug
6721 cuccgucacc acaacuuggu cuaugcuaca acaucucga cgcaagccu gcggcagaag
6781 aaggucaccu uugacagacu gcagguccug gacgaccacu accgggacgu gcucaaggag
6841 augaaggcga aggcguccac aguuaaggcu aaacuucuau ccguggagga agccuguaag
6901 cugacgcccc cacauucggc cagaucuaaa uuuggcuaug ggcaaagga cguccggaac
6961 cuauccagca aggccguuaa ccacaucgc uccgugugga ggacuugcu ggaagacacu
7021 gagacaccaa uugacaccac caucaggca aaaaugagg uuuucugcgu ccaaccagag
7081 aagggggcc gcaagccagc ucgccuuauc guauccag auuggggu ucgugugugc
7141 gagaaaaugg cccuuuacga uguggucucc accccuccuc aggccgugau gggcucuuca
7201 uacggauucc aauacucucc uggacagcgg gucgaguucc ggugaaugc cuggaaagcg
7261 aagaaaugcc cuaugggcuu cgcauaugac acccgcuguu ugacucaac ggucacugag
7321 aaugacaucc guuugagga gucaaucuac caauguugug acuuggcccc cgaagccaga
7381 caggccauaa ggucgcucac agagcggcuu acaucgggg cccccugac uaauucuaaa
7441 gggcagaacu gcggcuaucg ccggugccgc gcgagcggug uacugacgac cagcugcggu
7501 aauacccuca cauguuacuu gaaggccgcu gcggccuguc gagcugcgaa gcuccaggac
```

FIG. 1C

```
7561 ugcacgaugc ucguaugcgg agacgaccuu gucguuaucu gugaaagcgc ggggacccaa
7621 gaggacgagg cgagccuacg ggccuucacg gaggcuauga cuagauacuc ugccccccu
7681 ggggacccgc ccaaaccaga auacgacuug gaguugauaa caucaugcuc cuccaaugug
7741 ucagucgcgc acgaugcauc uggcaaaagg guguacuauc ucacccguga ccccaccacc
7801 ccccuugcgc gggcugcgug ggagacagcu agacacacuc cagucaauuc cuggcuaggc
7861 aacaucauca uguaugcgcc caccuugugg gcaaggauga uccugaugac ucauuucuuc
7921 uccauccuuc uagcucagga acaacuugaa aaagcccuag auugucagau cuacggggcc
7981 uguuacucca uugagccacu ugaccuaccu cagaucauuc aacgaccca uggccuuagc
8041 gcauuuucac uccauaguua cucuccaggu gagaucaaua ggugccuuc augccucagg
8101 aaacuugggg uaccgcccuu gcgagucugg agacaucggg ccagaagugu ccgcgcuagg
8161 cuacugaccc agggggggag ggcugccacu uguggcaagu accucuucaa cugggcagua
8221 aggaccaagc ucaaacucac uccaaucccg gcugcguccc aguuggauuu auccagcugg
8281 uucguugcug guuacagcgg gggagacaua uaucacagcc ugucucgugc ccgaccccgc
8341 ugguucaugu ggugccuacu ccuacuuucu guaggggu ag gcaucuaucu acuccccaau
8401 cgaugaaggu uggggu aaac acuccggccu cuuaggccau uccucucuu uuuuuguuu
8461 uuuuggguuu uuuuguuuuu uuucuuuuuu uuuuuuuuuu uuucuuuuuu ccuucuuccu
8521 uuucucuuuu uuucuucuuu aauggu ggcu ccaucuuagc ccuagucacg gcuagcugug
8581 aaagguccgu gagccgcaug acugcagaga gugcugauac uggccucucu gcagaucaug
8641 ugggucggca uggcaucucc accuccucgc gguccgaccu gggcauccga aggaggacgu
8701 cguccacucg gauggcuaag ggagagcucu ag
```

FIG. 1D

```
   1 gccagccccc gattgggggc gacactccac catagatcac tcccctgtga ggaactactg
  61 tcttcacgca gaaagcgtct agccatggcg ttagtatgag tgtcgtgcag cctccaggac
 121 ccccccctccc gggagagcca tagtggtctg cggaaccggt gagtacaccg gaattgccag
 181 gacgaccggg tcctttcttg gatcaaccc c tcaatgcct ggagatttgg gcgtgccccc
 241 gcgagactgc tagccgagta gtgttgggtc gcgaaaggcc ttgtggtact gcctgatagg
 301 gtgcttgcga gtgccccggg aggtctcgta gaccgtgcac catgagcacg aatcctaaac
 361 ctcaaagaaa aaccaaaggg cgcgccatgc acccagaaac gctggtgaaa gtaaaagatg
 421 ctgaagatca gttgggtgca cgagtgggtt acatcgaact ggatctcaac agcggtaaga
 481 tccttgagag ttttcgcccc gaagaacgtt tccaatgatg agcacttttt aaagttctgc
 541 tatgtggcgc ggtattatcc cgtattgacg ccgggcaaga gcaactcggt cgccgcatac
 601 actattctca gaatgacttg gttgagtact caccagtcac agaaaagcat cttacggatg
 661 gcatgacagt aagagaatta tgcagtgctg ccataaccat gagtgataac actgcggcca
 721 acttacttct gacaacgatc ggaggaccga aggagctaac cgcttttttg cacaacatgg
 781 gggatcatgt aactcgcctt gatcgttggg aaccggagct gaatgaagcc ataccaaacg
 841 acgagcgtga caccacgatg cctgtagcaa tggcaacaac gttgcgcaaa ctattaactg
 901 gcgaactact tactctagct tcccggcaac aattaataga ctggatggag gcggataaag
 961 ttgcaggacc acttctgcgc tcggcccttc cggctggctg gtttattgct gataaatctg
1021 gagccggtga gcgtgggtct cgcggtatca ttgcagcact ggggccagat ggtaagccct
1081 cccgtatcgt agttatctac acgacgggga gtcaggcaac tatggatgaa cgaaatagac
1141 agatcgctga gataggtgcc tcactgatta agcattggta agtttaaaca gaccacaacg
1201 gtttccctct agcgggatca attccgcccc tctccctccc ccccccctaa cgttactggc
1261 cgaagccgct tggaataagg ccggtgtgcg tttgtctata tgttattttc caccatattg
1321 ccgtcttttg gcaatgtgag ggcccggaaa cctggccctg tcttcttgac gagcattcct
1381 aggggtcttt ccctctcgc c aaaggaatg caaggtctgt tgaatgtcgt gaaggaagca
1441 gttcctctgg aagcttcttg aagacaaaca acgtctgtag cgacccttt g caggcagcgg
1501 aacccccac ctggcgacag gtgcctctgc ggccaaaagc cacgtgtata agatacacct
1561 gcaaaggcgg cacaacccca gtgccacgtt gtgagttgga tagttgtgga agagtcaaa
1621 tggctctcct caagcgtatt caacaagggg ctgaaggatg cccagaaggt accccattgt
1681 atgggatctg atctggggcc tcggtgcaca tgctttacat gtgtttagtc gaggttaaaa
1741 aacgtctagg ccccccgaac cacggggacg tggttttcct ttgaaaaaca cgataatacc
1801 atggcgccta ttacggccta ctcccaacag acgcgaggcc tacttggctg catcatcact
1861 agcctcacag gccgggacag gaaccaggtc gaggggggagg tccaagtggt ctccaccgca
1921 acacaatctt tcctggcgac ctgcgtcaat ggcgtgtgtt ggactgtcta tcatggtgcc
1981 ggctcaaaga cccttgccgg cccaaagggc ccaatcaccc aaatgtacac caatgtggac
2041 caggacctcg tcggctggca agcgcccccc ggggcgcgtt ccttgacacc atgcacctgc
2101 ggcagctcgg acctttactt ggtcacgagg catgccgatg tcattccggt gcgccggcgg
2161 ggcgacagca gggggagcct actctccccc aggcccgtct cctacttgaa gggctcttcg
2221 ggcggtccac tgctctgccc ctcggggcac gctgtgggca tctttcgggc tgccgtgtgc
2281 acccgagggg ttgcgaaggc ggtggacttt gtacccgtcg agtctatgga aaccactatg
2341 cggtccccgg tcttcacgga caactcgtcc cctccggccg taccgcagac attccaggtg
2401 gcccatctac acgcccctac tggtagcggc aagagcacta aggtgccggc tgcgtatgca
2461 gcccaagggt ataaggtgct tgtcctgaac ccgtccgtcg ccgccaccct aggtttcggg
```

FIG. 2A

```
2521  gcgtatatgt ctaaggcaca tggtatcgac cctaacatca gaaccggggt aaggaccatc
2581  accacgggtg cccccatcac gtactccacc tatggcaagt ttcttgccga cggtggttgc
2641  tctgggggcg cctatgacat cataatatgt gatgagtgcc actcaactga ctcgaccact
2701  atcctgggca tcggcacagt cctggaccaa gcggagacgg ctggagcgcg actcgtcgtg
2761  ctcgccaccg ctacgcctcc gggatcggtc accgtgccac atccaaacat cgaggaggtg
2821  gctctgtcca gcactggaga atccccttt tatggcaaag ccatccccat cgagaccatc
2881  aagggggga ggcacctcat tttctgccat tccaagaaga aatgtgatga gctcgccgcg
2941  aagctgtccg gcctcggact caatgctgta gcatattacc ggggccttga tgtatccgtc
3001  ataccaacta gcggagacgt cattgtcgta gaacggacg ctctaatgac gggctttacc
3061  ggcgatttcg actcagtgat cgactgcaat acatgtgtca cccagacagt cgacttcagc
3121  ctggacccga ccttcaccat tgagacgacg accgtgccac aagacgcggt gtcacgctcg
3181  cagcggcgag gcaggactgg taggggcagg atgggcattt acaggtttgt gactccagga
3241  gaacggccct cgggcatgtt cgattcctcg gttctgtgcg agtgctatga cgcgggctgt
3301  gcttggtacg agctcacgcc cgccgagacc tcagttaggt tgcgggctta cctaaacaca
3361  ccagggttgc ccgtctgcca ggaccatctg gagttctggg agagcgtctt tacaggcctc
3421  acccacatag acgcccattt cttgtcccag actaagcagg caggagacaa cttcccctac
3481  ctggtagcat accaggctac ggtgtgcgcc agggctcagg ctccacctcc atcgtgggac
3541  caaatgtgga agtgtctcat acggctaaag cctacgctgc acgggccaac gccctgctg
3601  tataggctgg gagccgttca aaacgaggtt actaccacac accccataac caaatacatc
3661  atggcatgca tgtcggctga cctggaggtc gtcacgagca cctgggtgct ggtaggcgga
3721  gtcctagcag ctctggccgc gtattgcctg acaacaggca gcgtggtcat tgtgggcagg
3781  atcatcttgt ccggaaagcc ggccatcatt cccgacaggg aagtccttta ccgggagttc
3841  gatgagatgg aagagtgcgc ctcacacctc ccttacatcg aacagggaat gcagctcgcc
3901  gaacaattca aacagaaggc aatcgggttg ctgcaaacag ccaccaagca agcggaggct
3961  gctgctcccg tggtggaatc caagtggcgg accctcgaag ccttctgggc gaagcatatg
4021  tggaatttca tcagcgggat acaatattta gcaggcttgt ccactctgcc tggcaacccc
4081  gcgatagcat cactgatggc attcacagcc tctatcacca gcccgctcac cacccaacat
4141  accctcctgt ttaacatcct gggggatgg gtggccgccc aacttgctcc tcccagcgct
4201  gcttctgctt tcgtaggcgc cggcatcgct ggagcggctg ttggcagcat aggccttggg
4261  aaggtgcttg tggatatttt ggcaggttat ggagcagggg tggcaggcgc gctcgtggcc
4321  tttaaggtca tgagcggcga gatgcctcc accgaggacc tggttaacct actccctgct
4381  atcctctccc ctggcgccct agtcgtcggg gtcgtgtgcg cagcgatact gcgtcggcac
4441  gtgggcccag gggaggggc tgtgcagtgg atgaaccggc tgatagcgtt cgcttcgcgg
4501  ggtaaccacg tctcccccac gcactatgtg cctgagagcg acgctgcagc acgtgtcact
4561  cagatcctct ctagtcttac catcactcag ctgctgaaga ggcttcacca gtggatcaac
4621  gaggactgct ccacgccatg ctccggctcg tggctaagag atgtttggga ttggatatgc
4681  acgtgttga ctgatttcaa gacctggctc cagtccaagc tcctgccgcg attgccggga
4741  gtccccttct tctcatgtca acgtgggtac aagggagtct ggcggggcga cggcatcatg
4801  caaccacct gcccatgtgg agcacagatc accggacatg tgaaaaacgg ttccatgagg
4861  atcgtggggc ctaggacctg tagtaacacg tggcatggaa cattccccat taacgcgtac
4921  accacggggcc cctgcacgcc ctccccggcg ccaaattatt ctagggcgct gtggcggtg
4981  gctgctgagg agtacgtgga ggttacgcgg gtgggggatt tccactacgt gacgggcatg
```

FIG. 2B

```
5041 accactgaca acgtaaagtg cccgtgtcag gttccggccc ccgaattctt cacagaagtg
5101 gatggggtgc ggttgcacag gtacgctcca gcgtgcaaac ccctcctacg ggaggaggtc
5161 acattcctgg tcgggctcaa tcaatacctg gttgggtcac agctcccatg cgagcccgaa
5221 ccggacgtag cagtgctcac ttccatgctc accgaccect cccacattac ggcggagacg
5281 gctaagcgta ggctggccag gggatctccc ccctccttgg ccagctcatc agctgcccag
5341 ctgtctgcgc cttccttgaa ggcaacatgc actacccgtc atgactcccc ggacgctgac
5401 ctcatcgagg ccaacctcct gtggcggcag gagatgggcg ggaacatcac ccgcgtggag
5461 tcagaaaata aggtagtaat tttggactct ttcgagccgc tccaagcgga ggaggatgag
5521 agggaagtat ccgttccggc ggagatcctg cggaggtcca ggaaattccc tcgagcgatg
5581 cccatatggg cacgcccgga ttacaaccct ccactgttag agtcctggaa ggacccggac
5641 tacgtccctc cagtggtaca cgggtgtcca ttgccgcctg ccaaggcccc tccgatacca
5701 cctccacgga ggaagaggac ggttgtcctg tcagaatcta ccgtgtcttc tgccttggcg
5761 gagctcgcca caaagacctt cggcagctcc gaatcgtcgg ccgtcgacag cggcacggca
5821 acggcctctc ctgaccagcc ctccgacgac ggcgacgcgg gatccgacgt tgagtcgtac
5881 tcctccatgc cccccttga ggggaaccg ggggaccccg atctcagtga cgggtcttgg
5941 tctaccgtga gcgaggaagc tagtgaggat gtcgtctgct gctcaatgtc gtatacatgg
6001 acaggcgcct tgatcacgcc atgcgctgcg gaggaaagca agctgcccat caacgcgttg
6061 agcaactctt tgctgcgcca ccataacatg gtttatgcca caacatctcg cagcgcaggc
6121 ctgcggcaga agaaggtcac ctttgacaga ctgcaagtcc tggacgacca ctaccgggac
6181 gtgctcaagg agatgaaggc gaaggcgtcc acagttaagg ctaaactcct atccgtagag
6241 gaagcctgca agctgacgcc cccacattcg gccaaatcca gtttggcta tggggcaaag
6301 gacgtccgga acctatccag caaggccgtt aaccacatcc actccgtgtg gaaggacttg
6361 ctggaagaca ctgtgacacc aattgacacc accatcatgg caaaaaatga ggttttctgt
6421 gtccaaccag agaaaggagg ccgtaagcca gcccgcctta tcgtattccc agatctggga
6481 gtccgtgtat gcgagaagat ggccctctat gatgtggtct ccaccttcc tcaggtcgtg
6541 atgggctcct catacggatt ccagtactct cctgggcagc gagtcgagtt cctggtgaat
6601 acctggaaat caaagaaaaa ccccatgggc ttttcatatg acactcgctg tttcgactca
6661 acggtcaccg agaacgacat ccgtgttgag gagtcaattt accaatgttg tgacttggcc
6721 cccgaagcca gacaggccat aaaatcgctc acagagcggc tttatatcgg gggtcctctg
6781 actaattcaa aagggcagaa ctgcggttat cgccggtgcc gcgcgagcgg cgtgctgacg
6841 actagctgcg gtaacaccct cacatgttac ttgaaggcct ctgcagcctg tcgagctgcg
6901 aagctccagg actgcacgat gctcgtgaac ggagacgacc ttgtcgttat ctgtgaaagc
6961 gcgggaaccc aagaggacgc ggcgagccta cgagtcttca cggaggctat gactaggtac
7021 tctgcccccc ccggggaccc gccccaacca gaatacgact tggagctgat aacatcatgt
7081 tcctccaatg tgtcggtcgc ccacgatgca tcaggcaaaa gggtgtacta cctcacccgt
7141 gatcccacca cccccctcgc acgggctgcg tgggaaacag ctagacacac tccagttaac
7201 tcctggctag gcaacattat catgtatgcg cccactttgt gggcaaggat gattctgatg
7261 actcacttct tctccatcct tctagcacag gagcaacttg aaaagcccct ggactgccag
7321 atctacgggg cctgttactc cattgagcca cttgacctac ctcagatcat tgaacgactc
7381 catggcctta gcgcattttc actccatagt tactctccag gtgagatcaa tagggtggct
7441 tcatgcctca ggaaacttgg ggtaccgccc ttgcgagctt ggagacaccg ggcccggaat
7501 gtccgcgcta ggcttctgtc cagaggaggc agggctgcca tatgtggcaa gtacctcttc
```

FIG. 2C

```
7561 aactgggcag taaggacaaa gcttaaactc actccaatag cggccgctgg ccggctggac
7621 ttgtccagct ggttcacggc tggctacagc gggggagaca tttatcacgg cgtgtctcat
7681 gcccggcccc gctggttctg gttttgccta ctcctgctcg ctgcaggaat aggcatctac
7741 ctcctcccca atcgatgaag gttggggtaa acactccggc ctcttaggcc atttcctctc
7801 tttttttttgt tttttgggt tttttgttt ttttctttt tttttttttt tttttctttt
7861 ttccttcttc cttttctctt ttttcttct ttaatggtgg ctccatctta gccctagtca
7921 cggctagctg tgaaaggtcc gtgagccgca tgactgcaga gagtgctgat actggcctct
7981 ctgcagatca tgtgggtcgg catggcatct ccacctcctc gcggtccgac ctgggcatcc
8041 gaaggaggac gtcgtccact cggatggcta agggagagct ctaga
```

FIG. 2D

A.
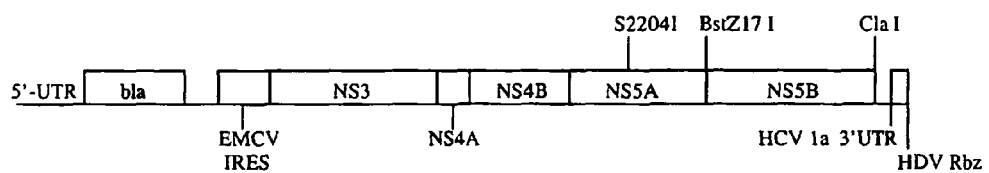
B.
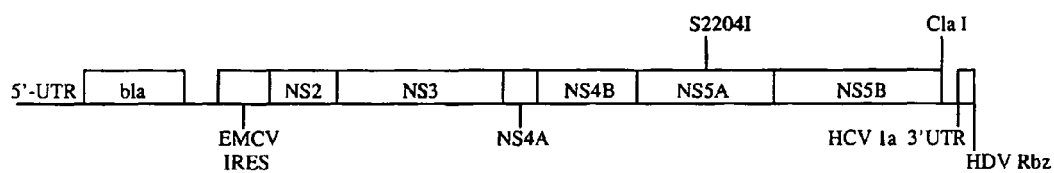
FIG. 3

HEPATITIS C VIRUS ASSAY SYSTEMS

CROSS-REFERENCE TO RELATED APPLICATIONS

The present application claims priority to provisional application U.S. Ser. No. 60/372,847, filed Apr. 16, 2002, hereby incorporated by reference herein.

BACKGROUND OF THE INVENTION

The references cited in the present application are not admitted to be prior art to the claimed invention.

It is estimated that about 3% of the world's population are infected with the Hepatitis C virus (HCV). (Wasley, et al., 2000. *Semin. Liver Dis.* 20, 1-16.) Exposure to HCV results in an overt acute disease in a small percentage of cases, while in most instances the virus establishes a chronic infection causing liver inflammation and slowly progresses into liver failure and cirrhosis. (Iwarson, 1994. *FEMS Microbiol. Rev.* 14, 201-204.) In addition, epiderniological surveys indicate an important role of HCV in the pathogenesis of hepatocellular carcinoma. (Kew, 1994. *FEMS Microbiol. Rev.* 14, 211-220, Alter, 1995. *Blood* 85, 1681-1695.)

The HCV genome consists of a single strand RNA of about 9.5 kb in length, encoding a precursor polyprotein of about 3000 amino acids. (Choo, et al., 1989. *Science* 244, 362-364, Choo, et al., 1989. *Science* 244, 359-362, Takamizawa, et al., 1991. *J. Virol.* 65, 1105-1113.) The HCV polyprotein contains the viral proteins in the order: C-E1-E2-p7-NS2-NS3-NS4A-NS4B-NS5A-NS5B.

Individual viral proteins are produced by proteolysis of the HCV polyprotein. Host cell proteases release the putative structural proteins C, E1, E2, and p7, and create the N-terminus of NS2 at amino acid 810. (Mizushima, et al., 1994. *J. Virol.* 68, 2731-2734, Hijikata, et al., 1993. *P.N.A.S. USA* 90, 10773-10777.)

The non-structural proteins NS3, NS4A, NS4B, NS5A and NS5B presumably form the virus replication machinery and are released from the polyprotein. A zinc-dependent protease associated with NS2 and the N-terminus of NS3 is responsible for cleavage between NS2 and NS3. (Grakoui, et al., 1993. *J. Virol.* 67, 1385-1395, Hijikata, et al., 1993. *P.N.A.S. USA* 90, 10773-10777.)

A distinct serine protease located in the N-terminal domain of NS3 is responsible for proteolytic cleavages at the NS3/NS4A, NS4A/NS4B, NS4B/NS5A and NS5A/NS5B junctions. (Barthenschlager, et al., 1993. *J. Virol.* 67, 3835-3844, Grakoui, et al., 1993. *Proc. Natl. Acad. Sci. USA* 90, 10583-10587, Tomei, et al., 1993. *J. Virol.* 67, 4017-4026.) RNA stimulated NTPase and helicase activities are located in the C-terminal domain of NS3.

NS4A provides a cofactor for NS3 protease activity. (Failla, et al., *J. Virol.* 1994. 68, 3753-3760, De Francesco, et al., U.S. Pat. No. 5,739,002.)

NS5A is a highly phosphorylated protein conferring interferon resistance. (De Francesco, et al., 2000. *Semin Liver Dis.,* 20(1), 69-83, Pawlotsky, 1999. *J. Viral Hepat. Suppl.* 1, 4748.)

NS5B provides an RNA-dependent RNA polymerase. (De Francesco, et al., International Publication Number WO 96/37619, Behrens, et al., 1996. *EMBO* 15, 12-22, Lohmann, et al., 1998. *Virology* 249, 108-118.)

SUMMARY OF THE INVENTION

The present invention features assays employing a beta-lactamase reporter system, an HCV replicon enhanced cell, and/or a chimeric HCV replicon containing a 3'UTR based on the HCV-1a 3' UTR. These features can be employed alone or together, and are preferably combined together to measure HCV replicon activity and the affect of compounds on such activity.

Thus, a first aspect of the present invention describes a method of measuring the ability of a compound to alter HCV replicon activity using a screening cell line comprising a first HCV replicon and a second HCV replicon. The first replicon comprises a selection sequence. The second replicon comprises a nucleotide sequence encoding for beta-lactamase. The method is performed using conditions supporting beta-lactamase activity. Such conditions provide the proper environment for beta-lactamase activity and include factors such as proper pH, temperature and buffer.

A selection sequence facilitates identification or isolation of cells containing the sequence. Examples of selection sequences include sequences encoding drug resistance and reporters compatible with cell sorting.

Another aspect of the present invention describes an HCV replicon enhanced cell comprising a first HCV replicon and a second HCV replicon. The first replicon comprises a selection sequence and is present in an amount compatible with replication of the second replicon. The second replicon is different from the first replicon and preferably encodes a reporter.

Another aspect of the present invention describes a method of producing an HCV replicon enhanced cell. The method comprises the steps of: (a) introducing into a cell a HCV replicon comprising a selection sequence; (b) obtaining a replicon enhanced cell; and (c) introducing into the replicon enhanced cell a replicon comprising a reporter.

Another aspect of the present invention describes an HCV replicon comprising a beta-lactamase reporter. In this aspect, the replicon does not contain a sequence coding for resistance to an agent that inhibits cell growth.

Another aspect of the present invention describes a chimeric HCV replicon containing an HCV-1a 3' UTR. The chimeric replicon contains one or more HCV regions from different HCV strains. Reference to strains includes subtypes, which may be clinical isolates. Examples of chimeric replicons include replicons formed from one or more strains classified as HCV-1a, where the replicon contains a 3' UTR from one strain and one or more HCV regions from a different strain(s); and the replicon being formed from two or more HCV strains classified in different groups, where the replicon contains a 3' HCV-1a UTR.

Preferably, the chimeric replicon contains the HCV-1a 3'UTR provided by bases 8407-8641 of SEQ. ID. NO. 1. The remainder of such a chimeric replicon contains one or more HCV regions, preferably a non-structural region, from a HCV strain not containing the HCV-1a 3' UTR provided by SEQ. ID. NO. 1.

Other features and advantages of the present invention are apparent from the additional descriptions provided herein including the different examples.

The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIGS. 1A-1D illustrate the HCV replicon of SEQ. ID. NO. 1. Sequences of all non-structural proteins are derived from con 1. The approximate location of different regions of SEQ. ID. NO. 1 are as follows:

1-341: 5'-nontranslated region
342-1178: HCV core-β-lactamase fusion protein
1225-1800: EMCV IRES
1801-2451: NS2
2452-4344: NS3
4345-4506: NS4A
4507-5289: NS4B
5290-6630: NS5A
6631-8406: NS5B
8407-8641: HCV(1a) 3'-nontranslated region
8642-8732: Hepatitis delta ribozyme.

FIGS. 2A-2D illustrate the HCV replicon of SEQ. ID. NO. 2. Sequences of all non-structural proteins are derived from con1. The approximate location of different regions of SEQ. ID. NO. 2 are as follows:

1-341: 5'-nontranslated region
342-1178: HCV core-β-lactamase fusion protein
1225-1800: EMCV IRES
1801-3696: NS3
3697-3858: NS4A
3859-4641: NS4B
4642-5982: NS5A
5983-7755: NS5B
5991-5996: BstZ17I restriction site
7751-7756: Cla I restriction site
7756-7993: HCV(1a) 3'-nontranslated region
7994-8085: Hepatitis delta ribozyme.

FIGS. 3A and 3B provide schematic diagrams of replicons of SEQ. ID. NO. 1 and SEQ. ID. NO. 2. Both replicons are derived from HCV con1 and contain the S2204I adaptive mutation in NS5A. An HCV genotype 1a 3'-UTR is present in both clones, and both have a hepatitis delta ribozyme that is autocleaved to yield native 3'-ends. (A) Structure of the replicon SEQ. ID. NO.1 which encodes NS2 through NS5B. (B) Structure of replicon SEQ. ID. NO. 2. which encodes NS3 through NS5B. The replicon of SEQ. ID. NO. 2 contains unique BstZ17 I and Cla I restriction sites at the 5' and 3' ends of the NSSB coding region, respectively, to facilitate subcloning of NSSB sequences for resistance phenotyping.

Figure 4:
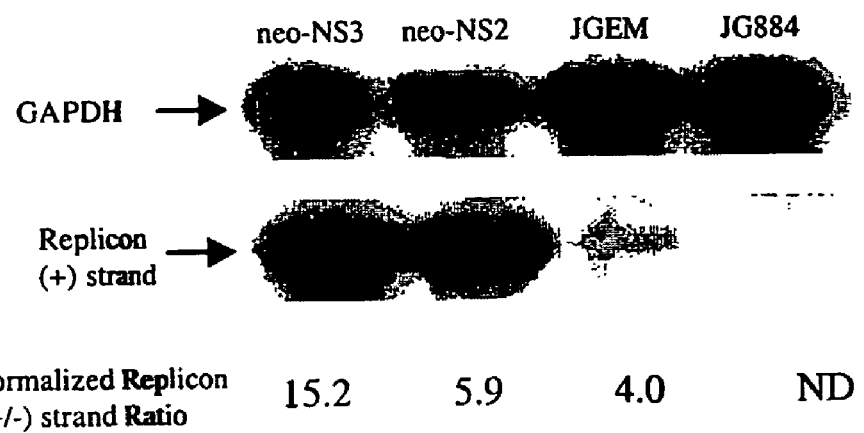

FIG. 4 illustrates quantitation of replicon RNA in different cell lines. Replicon RNA was quantitated using strand specific RNAse protection assays. Cellular GAPDH RNA and HCV replicon RNA of positive polarity are shown at the top and lower panels respectively. The ratios of positive to negative strand replicon RNA in each cell line are indicated at the bottom of the figure.

Figure 5:
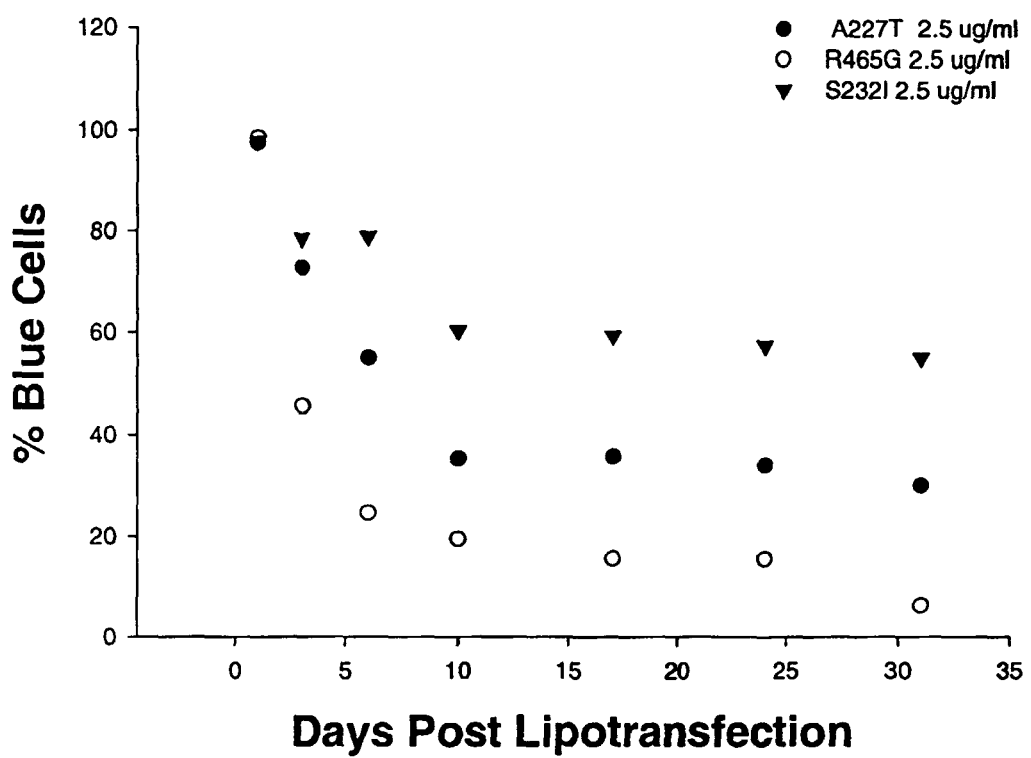

FIG. 5 illustrates stable maintenance of replicons harboring different adaptive mutations in partially cured JGEM cells.

Figure 6:
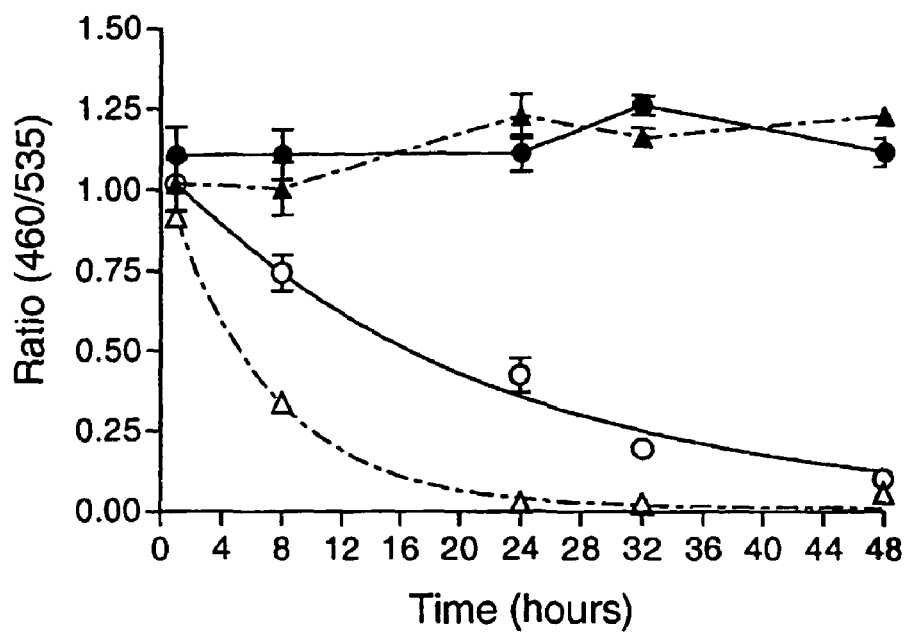

FIG. 6 illustrates persistence of beta-lactamase activity in the presence of inhibitor. The decay rates of beta-lactamase activity was measured in the presence of an NS5B inhibitor at 100% inhibitory dose (open symbols) either with (circles) or without (triangles) 0.5 µM clavulanic acid. Closed symbols represent cells without NS5B inhibitor.

DETAILED DESCRIPTION OF THE INVENTION

The present invention features assays employing a beta-lactamase reporter system, an HCV replicon enhanced cell, and/or a chimeric HCV replicon containing a HCV-1a 3' UTR. These different features are preferably employed together to evaluate the ability of a compound to inhibit HCV replication.

Compounds inhibiting HCV replication have research and therapeutic applications. Research applications include the study of HCV and the production of replicon enhanced cells. Therapeutic applications include using those compounds having appropriate pharmacological properties such as efficacy and lack of unacceptable toxicity to treat or inhibit onset of HCV in a patient.

I. Beta-Lactamase Reporter Systems

Assays employing a beta-lactamase reporter system can be used to measure the activity of a nucleic acid or polypeptide coupled to a beta-lactamase and the effect of a compound on such activity. Nucleic acid coupled to a beta-lactamase contains a target nucleotide region and a region encoding a beta-lactamase. Beta-lactamase is the byproduct of target nucleic acid expression and measuring Bla activity provides a mean to measure target nucleic acid activity.

The target nucleotide region is a region of interest and can provide regulatory activities or encode for a polypeptide. Reference to polypeptide and polypeptide region does not provide a size limitation and includes smaller length polypeptides, enzymatic proteins, structural proteins, and polyproteins.

Activities that can be measured using a target nucleotide region and a region encoding a beta-lactamase include one or more of the following: target nucleotide region production, target nucleotide region processing, target nucleotide region transport, activity of encoded for polypeptides involved in replication, and production of encoded for polypeptides. Nucleotide region transport includes extracellular transport that may be viral mediated.

A polypeptide coupled to beta-lactamase is a chimeric polypeptide containing a region of interest and a beta-lactamase. Polypeptide regions of interest include those providing enzymatic and structural proteins.

Polypeptide activities that can be measured using a beta-lactamase reporter system include one or more of the following: polypeptide production, polypeptide processing and polypeptide transport. Polypeptide transport includes extracellular transport that may be viral mediated.

A preferred target nucleic acid is an HCV replicon. HCV replicons containing a region encoding a beta-lactamase can be used to measure the effect of a compound on both HCV nucleic acid and HCV protein activity. HCV proteins are involved in processing the HCV polyprotein and in HCV replication. Inhibiting HCV proteins involved in HCV processing or more directly involved in HCV replication reduces the production of HCV replicons encoding beta-lactamase.

II. Beta-Lactamase Activity

Beta-lactamases are enzymes catalyzing the cleavage of the beta-lactam ring present in cephalosporins. Different naturally occurring beta-lactamases and functionally derivatives of naturally occurring beta-lactamases are well known in the art. References such as Ambler, *Phil. Trans R. Soc. Lond Ser.* B. 289:321-331, 1980, provide examples of naturally occurring β-lactamases.

Beta-lactamases that are functional derivatives of a naturally occurring beta-lactamase can be produced by altering a naturally occurring sequence to produce an enzyme retaining beta-lactamase activity. Examples of common alterations include substitutions, deletions, and additions of amino acids or amino acid regions.

One method of designing altered proteins is to take into account amino acid R-groups. An amino acid R group affects different properties of the amino acid such as physical size, charge, and hydrophobicity. Amino acids can be divided into different groups as follows: neutral and hydrophobic (alanine, valine, leucine, isoleucine, proline, tryptophan, phenylalanine, and methionine); neutral and polar (glycine, serine, threonine, tyrosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in polypeptide functioning.

Changes outside of different amino acid groups can also be made. Preferably, such changes are made taking into account the position of the amino acid to be substituted in the polypeptide. For example, arginine can substitute more freely for nonpolar amino acids in the interior of a polypeptide than glutamate because of its long aliphatic side chain. (See, Ausubel, *Current Protocols in Molecular Biology*, John Wiley, 1987-1998, Supplement 33 Appendix 1C.)

Derivatives can be produced to enhance intracellular activity. An example of such a derivative is TEM-1 beta-lactamase. (Kadonaga et al., *J. Biol. Chem.* 259:2149-2154, 1984.) TEM-1 beta-lactamase is a derivative of *E. coli* beta-lactamase where the signal sequence is deleted. The deletion of the signal sequence increases cytoplasmic accumulation.

Beta-lactamase encoding sequences can be incorporated into nucleic acids taking into account the genetic code. The translation of a particular codon into a particular amino acid is well known in the art (see, e.g., Lewin *GENES IV*, p. 119, Oxford University Press, 1990). Amino acids are encoded by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU.

III. Beta-Lactamase Assays

Intracellular beta-lactamase activity is preferably measured using a fluorogenic substrate that is cleaved by beta-lactamase. Preferred substrates are membrane permeant fluorogenic substrates that become membrane impermeant inside a cell, and that are cleaved by beta-lactamase to produce a detectable signal. Examples of such substrates are provided in Zlokarnik, et al., 1998. *Science* 279:84-88, and Tsien et al., U.S. Pat. No. 5,741,657.

In an embodiment of the present invention, a cell-permeant fluorescent β-lactamase substrate such as CCF2-AM or CCF4-AM (Aurora Biosciences, Inc., San Diego, Calif.) is loaded into a cell. These substrates contain an ester group facilitating transport across the cell membrane. Inside the cell, the ester group is cleaved rendering the substrate membrane impermeant. The intact substrates when stimulated with light of ~405 nm, emit green fluorescence (~530 nm) due to resonant energy transfer from a coumarin to fluorescein dye molecule. Cleavage of the substrate by beta-lactamase disrupts the resonance energy transfer and, the fluorescence emission changes to a blue color (~460 nm) of only the coumarin. The fluorescence emissions of the substrate present in the cells can be detected by, for example, fluorescence microscopy or by a fluorometer in conjunction with appropriate emission and excitation filters.

IV. Use Of Beta-Lactamase Inhibitor

Beta-lactamase inhibitors such as clavulanic acid can be used to enhance a beta-lactamase reporter system by being present throughout the assay. For example, clavulanic acid being present throughout an assay involving an HCV replicon beta-lactamase reporter sensitizes the assay towards HCV replication inhibitors.

Clavulanic acid can be used to enhance the signal-to-background ratio from the beta-lactamase reporter system wherein, a larger signal to noise ratio facilitates detection of HCV replication inhibitors by better reflecting changes in the intracellular concentration of beta-lactamase. Because clavulanic acid is an irreversible inhibitor, it is a more potent inhibitor of beta-lactamase at low enzyme concentrations than at high enzyme concentrations and therefore its inhibitory activity has a more pronounced effect in the background signal than in the foreground signal of the assay.

In different embodiments concerning the level of signal-to-background reduction, the beta-lactamase inhibitor is provided in an amount sufficient to enhance the signal-to-background ratio by 2 to 5 fold; the amount of inhibitor is about 10 nM to 1.0 μM; and/or the inhibitor is an irreversible inhibitor, preferably clavulanic acid.

V. HCV Replicons

An HCV replicon is an RNA molecule able to autonomously replicate in a cultured cell and produce detectable levels of one or more HCV proteins. The HCV replicon expresses the HCV derived components of the replication machinery and contains cis-elements required for replication in a cultured cell.

The production and use of HCV replicons, and the effect of different mutations on replicon activity are described in different references. (See, for example, Lohmann, et al., 1999. *Science* 285, 110-113, Bartenschlager, European Patent Application 1 043 399, published Oct. 11, 2000, Blight, et al., 2000. *Science* 290:1972-1974, Lohmann, et al., 2001. *Journal of Virology* 75:1437-1449, and Pietschmann, et al., 2001. *Journal of Virology* 75:1252-1264.)

The basic subunit of an HCV replicon encodes for a HCV NS3-NS4A-NS4B-NS5A-NS5B polyprotein (also referred to as NS3-NS5B) along with a suitable 5'-UTR-partial core (PC) region and 3' UTR. NS3-NS5B may contain different regions from different HCV strains. The 5'-UTR-PC region is made up of a 5'-UTR region and about 36 nucleotides of the beginning of the core. Additional regions may be present including those coding for HCV proteins or elements such as the complete core, E1, E2, p7 or NS2; and those coding for other types of proteins or elements such as a encephalomyocarditis virus (EMCV) internal ribosome entry site (IRES), a reporter protein, or a selection protein.

The HCV 5'-UTR-PC region provides an IRES for protein translation and elements needed for replication. The HCV 5'-UTR-PC region includes naturally occurring HCV 5'UTR extending about 36 nucleotides into a HCV core encoding region, and functional derivatives thereof. The IRES and PC can be present in different locations such as site downstream from a sequence encoding a selection protein, a reporter, protein, or an HCV polyprotein.

Functional derivatives of the 5'-UTR-PC region able to initiate translation and assist replication can be designed taking into account structural requirements for HCV translation initiation. (See, for example, Honda, et al., 1996. *Virology* 222, 31-42). The effect of different modifications to a 5' UTR-PC region can be determined using techniques measuring replicon activity.

In addition to the HCV 5' UTR-PC region, other types of IRES elements can also be present in the replicon. The other types of IRES elements can be present in different locations including immediately upstream the region encoding an HCV polyprotein. Examples of non-HCV IRES elements that can be used are the EMCV IRES, poliovirus IRES, and bovine viral diarrhea virus IRES.

The HCV 3' UTR assists HCV replication. HCV 3' UTR includes naturally occurring HCV 3' UTR and functional derivatives thereof. Naturally occurring 3' UTR's include a poly U tract and an additional region of about 100 nucleotides. (Tanaka, et al., 1996. *J. Virol.* 70, 3307-3312, Kolykhalov, et al., 1996. *J. Virol.* 70, 3363-3371.) At least in vivo, the 3' UTR appears to be essential for replication. (Kolykhalov, et al., 2000. *J. Virol.* 4, 2046-2051.) Examples of naturally occurring 3' UTR derivatives are described by Bartenschlager International Publication Number EP 1 043 399.

The NS3-NS5B polyprotein encoding region provides for a polyprotein that can be processed in a cell into different proteins. Suitable NS3-NS5B polyprotein sequences that may be part of a replicon include those present in different HCV strains and functional equivalents thereof resulting in the processing of NS3-NS5B to produce functional replication machinery. Proper processing can be measured by assaying, for example, HCV protein production.

An HCV replicon may contain non-HCV sequences in addition to HCV sequences. The additional sequences should not prevent replication and expression, and preferably serve a useful function. Sequences that can be used to serve a useful function include a selection sequence, a reporter sequence, transcription elements and translation elements.

A selection sequence in an HCV replicon facilitates the identification and/or isolation of a cell containing the replicon. Selection sequences providing for resistance to an agent that inhibits cell growth can be used in conjunction with some selective pressure that inhibits growth of cells not containing the selection sequence. Examples of selection sequences include sequences encoding for antibiotic resistance, and ribozymes; and reporters compatible with cell sorting such as green fluorescence protein and beta-lactamase.

Antibiotic resistance can be used in conjunction with an antibiotic to select for cells containing replicons. Examples of selection sequences providing for antibiotic resistance are sequences encoding resistance to neomycin, hygromycin, puromycin, or zeocin.

A ribozyme serving as a selection sequence can be used in conjunction with an inhibitory nucleic acid molecule that prevents cellular growth. The ribozyme recognizes and cleaves the inhibitory nucleic acid.

A reporter sequence can be used to detect replicon replication or protein expression. Preferred reporter proteins are enzymatic proteins whose presence can be detected by measuring product produced by the protein. Examples of reporter proteins include luciferase, beta-lactamase, secretory alkaline phosphatase, beta-glucuronidase, green fluorescent protein and its derivatives. In addition, a reporter nucleic acid sequence can be used to provide a reference sequence that can be targeted by a complementary nucleic acid. Hybridization of the complementary nucleic acid to its target can be determined using standard techniques.

Replicons containing reporter sequences may or may not also contain a selection sequence. Selection sequences providing resistance to an agent that inhibits cell growth can be used in conjunction with selective pressure to select for cells maintaining the replicon. The Examples provides below illustrate that replicons containing a beta-lactamase reporter sequences are sufficiently maintained in the absence of selective pressure. In an embodiment of the present invention the replicon contains a reporter sequence (preferably, beta-lactamase), and does not contain a sequence coding for resistance to an agent that inhibits cell growth.

Additional sequences can be part of the same cistron as the HCV polyprotein or can be a separate cistron. If part of the same cistron, additional sequences coding for a protein should result in a product that is either active as a chimeric protein or is cleaved inside a cell so it is separated from HCV protein.

Selection and reporter sequences encoding a protein when present as a separate cistron should be associated with elements needed for translation. Such elements include an IRES 5' to the selection or reporter sequence.

A preferred construct is a bicistronic replicon, where one cistron encodes for a selection or reporter sequence and the second cistron encodes for HCV proteins. More preferably, the first cistron contain a HCV 5'-UTR-PC region joined to the selection or reporter sequence; and the second cistron contains the EMCV internal ribosome entry site, NS2-NS5B or NS3-NS5B, and a 3' UTR. Examples of bicistronic constructs are illustrated by SEQ. ID. NOs. 1 and 2.

Preferred cells for use with a HCV replicon are Huh-7 cells and Huh-7 derived cells. "Huh-7 derived cells" are cells produced starting with Huh-7 cells and introducing one or more phenotypic and/or genotypic modifications.

VI. HCV Replicon Sequences

HCV sequences for use in HCV replicons include HCV sequences present in different HCV strains and functional derivatives thereof. Functional derivatives can process the HCV polyprotein and provide for HCV replication.

Replicon activity from naturally occurring sequences providing for little or no detectable replicon activity in a cell can be enhanced by producing functional derivatives containing adaptive mutations. Adaptive mutations and techniques for selecting for adaptive mutations are well known in the art. (See, for example, Lohmann, et al., 1999. *Science* 285, 110-113, Bartenschlager, European Patent Application 1 043 399, published Oct. 11, 2000, Blight, et al., 2000. *Science* 290: 1972-1974, Lohmann, et al., 2001. *Journal of Virology*

75:1437-1449, and Pietschmann, et al., 2001. *Journal of Virology* 75:1252-1264, 2001.)

Numerous examples of naturally occurring HCV isolates are well known in the art. HCV isolates can be classified into the following six major genotypes comprising one or more subtypes: HCV-1/(1a, 1b, 1c), HCV-2/(2a, 2b, 2c), HCV-3/(3a, 3b, 10a), HCV-4/(4a), HCV-5/(5a) and HCV-6/(6a, 6b, 7b, 8b, 9a, 11a). (Simmonds, 2001. *J. Gen. Virol.*, 82, 693-712.) Examples of HCV sequences have been deposited in GenBank and described in various publications. (See, for example, Chamberlain, et al., 1997. *J. Gen. Virol.*, 78, 1341-1347).

VII. Chimeric HCV Replicons and Resistance Phenotyping

Chimeric HCV replicons contain HCV regions from different HCV strains and can be used, for example, to measure the effect of a compound on HCV activity and to provide a template for HCV resistance phenotyping. The starting template for HCV resistance phenotyping is a functional replicon. One or more different regions of the functional replicon can be replaced with an HCV region from a different strain, including HCV obtained from a patient infected with the virus.

The template used for HCV resistance phenotyping can contain regions from different HCV strains. Preferably, the template contains a HCV-1a 3' UTR. Bases 8407-8641 of SEQ. ID. NO. 1 provide the nucleotide sequence of the HCV-1a 3' UTR.

HCV resistance phenotyping can be performed by examining the sensitivity of different HCV targets isolated from a clinical sample to experimental or approved HCV drugs using a chimeric replicon. HCV targets that can be analyzed include HCV encoded enzymes such as NS2/3 protease, NS3 protease, NS3 helicase, and NS5B, as well as polynucleotide regions important for HCV replication. In different embodiments concerning HCV chimeric replicons, the replicon comprises:

a) a HCV 3'UTR, preferably HCV-1a UTR, b) HCV non structural proteins from any one genotype or any combination of genotypes as long as the combination supports HCV replication, different HCV genotypes include HCV-1, HCV-2, HCV-3, HCV-4, HCV-5, and HCV-6; preferably, the non-structural regions contain one region from a clinical isolate;

c) restriction sites that are silent with respect to coding that facilitate introduction of HCV sequences obtained from a clinical isolate; and d) a reporter gene, preferably beta-lactamase.

Resistance phenotyping can be performed by isolating an HCV target region from a clinical isolate, and transferring the region to a template replicon. An example of a procedure for constructing a chimeric HCV replicon for use in resistance phenotyping is as follows:

a) Isolation and purification: isolation and purification of HCV genomic RNAs from infected patient serum can be achieved using well known techniques. (Examples of such techniques are described in Chamberlain, et. al., 1997. *J. Gen. Virol.*, 78, 1341-1347, Grahovac, et. al., 2001. *J. Clin. Virol.* 20, 85-89, Castelain, et al., 2002. *JID* 185, 573-583, Farci, et. al., 2002. *PNAS* 99, 3081-3086.)

b) Reverse transcription of HCV RNA and PCR amplification of HCV DNA: Oligonucleotide primers specific to the highly conserved 3'-end of the 3'-non-translated regions can be used to generate cDNA copies of genomic RNA;

c) Amplification of desired target sequences. Polymerase chain reaction amplification can performed to amplify the target sequence using primers 5' and 3' of the target sequence. The primers preferably contain restriction sites that facilitate cloning. Examples of useful restriction sites include BstZ17 I and Cla I and Bcl I; and d) Subcloning of target sequence: Restriction enzymes are used to subclone the target sequence into a HCV replicon.

Two examples of HCV template sequences useful for resistance phenotyping are provided by SEQ. ID. NO. 1 and SEQ. ID. NO. 2. SEQ. ID. NO. 1 contains an NS2-NS5B region from HCV-1b consensus (con-1) while SEQ. ID. NO. 2 contains a NS3-NS5B region from HCV-1b consensus (con-1). SEQ. ID. NO. 2 also contains useful restriction sites for subcloning NS5B. SEQ. ID. NOs. 1 and 2 both contain a beta-lactamase reporter and a HCV-1a 3' UTR.

In different embodiments of the present invention, one or more HCV regions from SEQ. ID. NOs. 1 or 2 are replaced with an HCV region from a clinical isolate. Preferably, the region from the clinical isolate is either NS2/3 protease, NS3 protease, NS3 helicase, NS5B or a combination thereof.

VIII. Replicon Enhanced Cells

HCV replicon enhanced cells provide a preferred system for measuring HCV replicon activity. HCV replicon enhanced cells can be isolated based on their ability to support replication of a first replicon and the resulting cell population supports more efficient replication of a second replicon compared to parental cells.

The replicon enhanced cell supports chronic or persistent replication of the second HCV replicon. Enhanced cells may or may not contain the first HCV replicon used obtain the replicon enhanced cell.

The first HCV replicon is defined as the replicon used to select the enhanced cell population and the second replicon is defined as the replicon used to measure HCV replication. Preferably, replicon enhanced cells contain a first HCV replicon having a drug resistance gene and a second HCV replicon having a reporter. The first replicon is present in an amount (copy number) compatible with efficient replication of the second HCV replicon. The combination of the two replicons in a replicon enhanced cell is particularly useful for high throughput screening.

Different HCV replicons can be constructed for use as the first replicon. A drug resistance gene can be used to isolate cells that support replication of the first replicon. Alternatively, the first replicon can encode a reporter gene that is compatible with cell sorting which allows isolation of cells that support replication of the first replicon.

The first replicon, if present in a cell containing the second replicon, should be present in an amount compatible with efficient replication of the second HCV replicon. The enhanced phenotype of a replicon enchanced cell can be masked or inhibited if the copy number of the first replicon is too high.

If needed, the copy number of the first replicon can be reduced by treating cells with inhibitors of HCV replication or by using cell culture conditions that are not compatible with replicon replication. The latter includes maintaining the cells at high cell densities for prolonged periods of time. The second replicon can be used to monitor HCV replication in enhanced cells.

Inhibitors of HCV replicon replication include IFN-α and HCV inhibitor compounds targeting a HCV protein. Examples of HCV inhibitory compounds are described in Llinas-Brunet, et al., 2000. *Bioorg Med Chem. Lett.* 10(20), 2267-2270.

The first replicon can also be made less active to reduce its copy number. A less active first replicon can be produced in different ways such as by employing regulatory elements or HCV coding sequences that provide for less activity. Regulatory elements that can be altered include ribosome binding sequences, 5' UTR, and 3 'UTR sequences. The activity of a replicon can readily be tested by, for example, measuring HCV nucleic acid or protein production.

Different HCV replicons can be constructed for use as the second replicon. The second replicon in addition to containing an HCV sequence preferably contains a reporter sequence. More preferably, the second replicon contains a reporter sequence such as beta-lactamase, beta galactosidase, green fluorescence protein or luciferase.

IX. Detection Methods

Methods for detecting replicon activity include those measuring the production or activity of replicon RNA and encoded protein. Measuring includes qualitative and quantitative analysis. Preferably, replicon activity is measured using a reporter protein. A preferred reporter system is the beta-lactamase reporter system.

Beta-lactamase activity can be measured, for example, by direct visualization of cells using a fluorescence microscope. Quantitation of HCV replication can be accomplished using a CCD camera that acquires digital images and suitable software that quantitates the number of blue and green cells present in such images. This method quantitates the number of cells in a population that harbors HCV replicons expressing beta-lactamase and this measurement is typically expressed as percentage blue cells (% Blue cells).

Another method for measuring beta-lactamase activity is using a fluorescence plate reader that quantitates the amount and green (~530 nm) or blue (~460 nm) fluorescence emitted by cells stimulated with light of ~405 nm. This method can be used for high throughput screening.

Quantitation of beta-lactamase activity can also be accomplished by FACS. This method quantitates the number of blue and green cells in a given cell population as well as the amount of blue and green fluorescence. Instruments capable of cell sorting can be used to isolate cells harboring HCV replicons expressing beta-lactamase.

Techniques suitable for measuring RNA production include those detecting the presence or activity of RNA. The presence of RNA can be detected using, for example, complementary hybridization probes or quantitative PCR. Techniques for measuring hybridization between complementary nucleic acid and quantitative PCR are well known in the art. (See for example, Ausubel, *Current Protocols in Molecular Biology*, John Wiley, 1987-1998, Sambrook, et al., *Molecular Cloning, A Laboratory Manual*, $2^{nd}$ Edition, Cold Spring Harbor Laboratory Press, 1989, and U.S. Pat. No. 5,731,148.)

RNA enzymatic activity can be provided to the replicon by using a ribozyme sequence. Ribozyme activity can be measured using techniques detecting the ability of the ribozyme to cleave a target sequence.

Techniques for measuring protein production include those detecting the presence or activity of a produced protein. The presence of a particular protein can be determined by, for example, immunological techniques. Protein activity can be measured based on the activity of an HCV protein or a reporter protein sequence.

Techniques for measuring HCV protein activity vary depending upon the protein that is measured. Techniques for measuring the activity of different non-structural proteins such as NS2/3, NS3, and NS5B, are well known in the art. (See, for example, references provided in the Background of the Invention.)

Assays measuring replicon activity also include those detecting virion production from a replicon that produces a virion; and those detecting a cytopathic effect from a replicon producing proteins exerting such an effect. Cytopathic effects can be detected by assays suitable to measure cell viability.

Assays measuring replicon activity can be used to evaluate the ability of a compound to modulate HCV activities. Such assays can be carried out by providing one or more test compounds to a cell expressing an HCV replicon and measuring the effect of the compound on replicon activity. If a preparation containing more than one compound is used and found to modulate replicon activity, individual compounds or smaller groups of compounds can be tested to identify replicon active compounds.

HCV inhibitory compounds can be used to produce replicon enhanced cells and compounds having the appropriate pharmacological properties may be therapeutic compounds. The ability of a compound to serve as a therapeutic compound can be confirmed using animal models such as a chimpanzee to measure efficacy and toxicity.

X. Examples

Examples are provided below to further illustrate different features of the present invention. The examples also illustrate useful methodology for practicing the invention. These examples do not limit the claimed invention.

Example 1

Production of Replicon Enhanced Cells

This example illustrates the production of replicon enhanced cells. It is not necessary to cure cells from the first replicon to obtain a cell population that is enhanced for replication of a second replicon. A preferred method to achieve this is to use a replicon (first replicon) with replication properties and replicon copy number that are compatible with enhanced replication of a second replicon.

Replicons used in the Example section have the general gene organization: HCV 5'UTR-drug resistance and/or reporter-EMCV IRES-HCV NS proteins-HCV 3'UTR. The replicon nomenclature used in the examples is as follows: the drug resistance and/or reporter gene under control of the HCV RES is indicated first, the start of the HCV polyprotein is indicated next and the presence of adaptive mutations is indicated last. For example, a replicon harboring the S2204I adaptive mutation, expressing the neo gene and containing the NS3-NS5B HCV NS region is referred to as neo-NS3/si. Replicons expressing Bla instead of $neo^r$ and containing the NS2-NS5B HCV NS region are referred to as Bla-NS2/si.

The activity of a beta-lactamase replicon (bla-NS3/si) and a replication deficient replicon (bla-NS3/si/gaa), was compared in parental Huh-7 cells, neo-NS3 cells (Huh-7 cells harboring neo-NS2 replicons), neo-NS2 (Huh-7 enhanced cells harboring neo-NS2 replicons) partially cured neo-NS2 cells harboring a reduced number of neo-NS2 replicons and cured neo-NS2 cells that do not contain replicons. Neo-NS2 cells were partially cured using interferon alpha and are referred to as JGEM cells. Neo-NS2 cells were completely cured using a potent inhibitor of HCV replication and are referred to in the examples below as JG884 cells.

Quantitation of the beta-lactamase reporter was used to measure HCV sub-genomic replication and is expressed as the percentage of beta-lactamase positive cells (% blue cells). The percentage of blue cells (% BC) at 24 hours after transfection is close to 100% in both cell lines indicating similar transfection efficiencies (Table 1). The % BC at days 3 & 6 post transfection is a measure of persistent replication.

The experiment described in Table 1 shows that the bla-NS3/si/gaa replicon did not replicate in any of the cell lines analyzed but replication of the bla-NS3/si replicon was readily detected in all cell lines both at day 3 and day 6. The activity of the bla-NS3/si replicon was significantly lower in Huh-7 and neo-NS3 cells than in the neo-NS2 cell lines.

Importantly, the replication efficiency of the bla-NS3/si replicon was comparable in neo-NS2, JGEM, and JG884 cells demonstrating that cells harboring neo-NS2 replicons do not have to be cured to support enhanced replication of a second replicon. In contrast, the activity of the bla-NS3/si replicon in the neo-NS3 cell line was similar to that observed in Huh-7 cells indicating that neo-NS3 cells were not enhanced (Table 1).

TABLE 1

Cells Harboring Neo-NS2 Replicons Are Enhanced For Replication Of A Replicon Expressing Beta-Lactamase

| Cell type | % Blue Cells | | |
|---|---|---|---|
| | Day 1 | Day 3 | Day 6 |
| Huh7 | 69 | 4 | 3 |
| Neo-NS3/si | 76 | 17 | 7 |
| Neo-NS2/si | 81 | 18 | 18 |
| JGEM | 81 | 30 | 28 |
| JG 884 | 75 | 12 | 24 |

Quantitation of replicon RNA in the different cell lines indicate that neo-NS3 cells produce significantly more RNA per cell than neo-NS2 cells suggesting that the replicon copy number in neo-NS3 cells might be too high for efficient replication of a second replicon (FIG. 4). These observations support the hypothesis that there is a threshold of RNA copy number above which cells are not able to efficiently support replication of a second replicon.

The enhanced phenotype of JGEM and JG884 cells is similar to neo-NS2 cells and is manifested as both increased permissiveness (i.e., a greater percentage of transfected cells support replication) and increased persistence (ie., replicon maintenance). The enhanced phenotype is not dependent on the sequence of the second replicon. The observation that JGEM cells support enhanced replication of replicons harboring adaptive mutants S2321 (SI), A227T (AT) and, R465G (RG) (FIG. 5) is in agreement with this notion. Moreover, JGEM (FIG. 5) but not Huh-7 cells (not shown) can maintain persistent replication of all three replicons for multiple cell passages without the need of drug selection pressure.

Example 2

Use Of Enhanced Cells to Generate a Cell Line to Screen Inhibitors of HCV Replication Examples of techniques that can be employed to create a stable cell line harboring a second replicon expressing the beta-lactamase reporter and assaying for activity is provided in this example. Replicon enhanced cells containing a first replicon can be produced as described in Example 1.

Enhanced Huh-7 cells are transfected with HCV replicon RNA encoding beta-lactamase. The resulting cell population is expanded using standard cell culture conditions (DMEM supplemented with 10% FCS, 2 mM L-glutamine, 1×non-essential amino acids, Pen/Strep) until the desired number of replicon harboring cells is obtained.

An alternative approach involves cell sorting. Cell sorting can be performed, for example, by separating cell harboring replicons three to six days after transfection from cells that do not harbor the replicon using flow cytometry assisted cell sorting. The population of cells stably maintaining the replicon expressing beta-lactamase is expanded using standard cell culture techniques until sufficient cells ($>2\times10^9$) to carry out the screen is obtained. Replicon harboring cells are then aliquoted, frozen and stored in liquid nitrogen.

Prior to use, frozen cells are thawed fresh in the morning of the assay or the day before and diluted in pre-warmed media to 40,000 cells/ml. Cell suspension (50 µl) is plated into 384-well micro-titer plates. The cells are allowed to recover for at least 6 hours at 37° C. in the plates before beginning an assay. 1 µl of 25 µM clavulanic acid in PBS and 0.25 µl of 500 µM test compounds in DMSO are added to the cells. The assay cell plates are then incubated for 24 hours at 37° C. To the assay plate, 10 µl of 6×CCF4/AM substrate in loading buffer is added with a Multidrop (Labsystems), and the plate incubated for 90 minutes at ambient temperature. The plate is then read from the bottom on a Teacn Spectrafluor Plus (340 nm excitation, 460 nm and 530 nm emissions).

Example 3

Use of Clavulanic Acid to Sensitize an HCV Replicon Beta-Lactamase Assay to Inhibitors of HCV Replication In the example described below, clavulanic acid is present throughout the assay at a concentration that slightly reduces beta-lactamase activity instead of using it at high concentration that would complete inhibit beta-lactamase activity. Because clavulanic acid is an irreversible inhibitor, it is a more potent inhibitor of beta-lactamase at low enzyme concentrations than at high enzyme concentrations and therefore its inhibitory activity has a more pronounced effect in the background signal than in the foreground signal which in turn explains the enhancement of the signal-to-background ratio from the beta-lactamase reporter.

Table 2 provides results obtained using different concentrations of clavulanic acid and an HCV NS5B inhibitor.

TABLE 2

Improved Potency Of An NS5B Inhibitor In The Presence Of Increasing Concentrations Of Clavulanic Acid

| [CA] µM | S/B | Δ | $IC_{50}$ µM |
|---|---|---|---|
| 0.00 | 3.5 | 1.23 | 1.3 |
| 0.13 | 5.7 | 1.22 | 0.94 |
| 0.25 | 6.0 | 1.17 | 0.84 |
| 0.50 | 6.3 | 0.97 | 0.54 |
| 1.00 | 5.4 | 0.81 | 0.42 |

The experiment in FIG. 6 shows that in the absence of clavulanic acid, the half-life of beta-lactamase activity in the replicon assay is approximately 14.9 hours but in the presence of 0.5 µM of clavulanic acid the half life of beta-lactamase activity is 4.7 hours. The lower half life of beta-lactamase in the presence of clavulanic acid improves the signal to noise ratio of a 24 hour assay.

Example 4

Use of a Beta-Lactamase Reporter System to Enrich Cell Populations Harboring HCV Replicons JGEM cells were lipotransfected with bla-NS2/si (BK 3'-UTR) replicon RNA using DMRIE-C (transfection reagent, Invitrogen Life Technologies) and expanded under standard growth conditions. Cells were stained with CCF4/AM for 90 minutes, dissociated from the flask with 0.25% trypsin/1 mM EDTA, and then suspended in sort buffer (PBS with 0.1% bovine serum albumin and pen/strep).

Cells were then sorted using Becton-Dickenson FACS Vantage SE cell sorter equipped with Coherent Innova 70C-4 (488 nm) and Coherent 302C Krypton (407 nm) lasers. Optical filters used on the cell sorter were 530/30 and 450/30 bandpass filters separated by a 490 dichroic mirror. Cells were sorted at a rate of 10,000 cells/s.

Cells staining positive for beta-lactamase expression were collected in complete medium containing 20% fetal calf serum. Medium was replaced the following day with complete medium containing 10% FCS. Cells were assayed for % blue cells by digital image processing at the indicated intervals. Cells maintained replicon for at least two weeks as indicated by the high percentage of cells that stain positive for the beta-lactamase reporter (Table 3).

TABLE 3

Enrichment Of A Cell Population Harboring An HCV Replicon Expressing Beta-Lactamase

| Day Post Sort | % Blue Cells |
| --- | --- |
| Pre-sort | 10 |
| Day 1 | 83 |
| Day 4 | 89 |
| Day 8 | 82 |
| Day 14 | 73 |
| Day 15 | 75 |

Example 5

Use of a Beta-Lactamase Reporter System to Identify Functional HCV Sequences HCV BK is a genotype 1b clone that is infectious in chimpanzees. BK replicons with and without the NS5A S2204I adaptive mutation were generated and tested for their ability to replicate using the beta-lactamase reporter. The replicon without the S2204I adaptive mutation failed to replicate in JGEM cells, while the replicon with the mutation replicated with modest efficiency.

A series of BK and con1 chimeras were generated to identify the region(s) that accounts for the different replicative activities of the two replicons. JGEM cells were lipotransfected with chimeric replicon RNAs and then cultured for 4 days under standard growth conditions. As shown in Table 4, replacement of the BK NS3 sequence with that from the con1 replicon resulted in a dramatic improvement in replication. In other BK/con1 chimeras, most of the differences in replication efficiency tracked with the NS3 sequence used while other parts of the genome had more modest or no effects on the observed differences in replication efficiency.

TABLE 4

Identification Of Functional HCV Sequence Using Beta-Lactamase Reporter System

| Replicon | % Blue Cells |
| --- | --- |
| Bla-BK NS3 | 0.05 |
| Bla-Bk NS3/S1 | 2.05 |
| Bla-BK NS3 with con 1 NS3 | 0.13 |
| Bla-BK NS3/S1 with con 1 NS3 | 49.9 |
| Bla-NS3/S1 | 44.2 |
| Bla-NS3/S1 with BK NS3 | 0.71 |

Example 6

Production of Functional Chimeric Replicons for Resistance Phenotyping

This example illustrates resistance phenotyping with NS5B. BstZ17 I and Cla I restrictions sites were introduced at the 5'-and 3'-ends of the NS5B coding region, respectively. The nucleotide substitutions made to introduce these restriction sites do not affect amino acid coding. The BstZ17 I and Cla I sites are unique in the resulting construct and facilitate rapid subcloning of NS5B sequences from clinical isolates for phenotypic analysis. As shown in Table 5, the nucleotide changes required to introduce the restriction sites do not affect replication.

Viral RNA was purified from 140 μl of infected patient serum ($10^3$-$10^6$ copies/ml) using the Qiagen viral RNA purification kit according to the manufacturer's directions followed by phenol:chloroform extraction and ethanol precipitation. cDNAs were generated by reverse transcription of 1/20 to 1/5 of the sample using a poly(A) oligonucleotide primer and Superscript II reverse transcriptase (Gibco-BRL) according to the manufacturer's guidelines.

NS5B coding regions were amplified by nested PCR using Expand High Fidelity polymerase (Roche). The initial amplification reaction was carried out using a primer that anneals immediately upstream of the NS5B coding region and the poly(A) primer used for reverse transcription. The second amplification used primers (sequences) that anneal at the 5'- and 3'-ends of the NS5B coding region internal to the primers used in the initial PCR reaction.

Amplification products were cloned directly into pGEM T-vector (Promega). The NS5B coding regions were subsequently amplified using a sense primer that included Bcl I restriction site and an antisense primer designed to introduce a Cla I site at the 3'-end. Amplification products were subcloned into the corresponding sites of SEQ. ID. NO. 2 to generate chimeric viruses containing the NS5B sequences derived from the clinical samples.

Replication of the chimeric replicons was characterized by using the beta-lactamase reporter assay as described above. As shown in Table 5, functional replicons with NS5B sequences from another genotype 1b isolate and from a genotype 1a isolate were functional in the context of the resistance phenotyping replicon.

TABLE 5

Functional Chimeric Replicons For Resistance Phenotyping

| Replicon | % Blue Cells |
| --- | --- |
| Bla-NS3/si con1 NS5B (Cla I) | 34.0 |
| Bla-NS3/si (BstZ17 1) con1 NS5B (Cla I) | 33.2 |

TABLE 5-continued

Functional Chimeric Replicons For Resistance Phenotyping

| Replicon | % Blue Cells |
|---|---|
| Bla-NS3/si (BstZ17 1) HC(1b) NS5B (Cla I) | 30.0 |
| Bla-NS3/si (BstZ17 1) RB(1a) NS5B (Cla I) | 6.3 |
| Bla-NS3/si (GAA) | 0.3 |

Example 7

Importance of 3'-UTR

NS2 replicon constructs that expressed a beta-lactamase reporter and that contained either the con1 or HCV 1a 3'-UTR were generated using techniques well known in the art. Replication of the resulting replicons was analyzed by digital image processing or using a fluorescent plate reader. As shown in Table 6, the replicon containing the HCV 1a 3'-UTR replicates more efficiently than the corresponding replicon containing the con1 3'-UTR.

TABLE 6

Enhancement Of Replication With HCV 1a 3'-UTR

| Replicon | % Blue Cells | Em460/Em530 × 100 |
|---|---|---|
| Bla-NS2/BK NS5B with con1 3'-UTR | 11.3 | 14.0 |
| Bla-NS2/BK NS5B with 1a 3'UTR | 32.5 | 41.2 |
| Bla-NS2(con1)/si with con1 3'UTR | 23.9 | 22.3 |
| Bla-NS2(con1)/si with 1a 3' UTR | 42.6 | 56.3 |
| Bla-NS2/si/GAA | 0.2 | 5.3 |
| Mock | 0.0 | 0.0 |

Other embodiments are within the following claims. While several embodiments have been shown and described, various modifications may be made without departing from the spirit and scope of the present invention.

---

What is claimed is:

1. A chimeric HCV replicon consisting of a modified version of SEQ ID NO: 2, wherein said said modified version of SEQ ID NO: 2 contains SEQ ID NO: 2 modified by replacing the NS5B region with a NS5B region from a clinical isolate of HCV.

2. A chimeric HCV replicon of SEQ ID NO:2, wherein at least a portion of nucleotides encoding a non-structural HCV polypeptide is replaced by a corresponding portion of nucleotides from a clinical isolate of HCV.

3. The chimeric HCV replicon of claim 2, wherein the non-structural HCV polypeptide is selected from the group consisting of NS2/3 protease, NS3 protease, NS3 helicase, and NS5B polymerase.

4. The chimeric HCV replicon of claim 3, wherein the non-structural HCV polypeptide is NS5B.

5. A chimeric HCV replicon consisting of SEQ ID NO:2.

* * * * *

SEQUENCE LISTING

<160> NUMBER OF SEQ ID NOS: 2

<210> SEQ ID NO 1
<211> LENGTH: 8732
<212> TYPE: RNA
<213> ORGANISM: Artificial Sequence
<220> FEATURE:
<223> OTHER INFORMATION: HCV replicon

<400> SEQUENCE: 1

```
gccagccccc gauuggggggc gacacuccac cauagaucac uccccuguga ggaacuacug      60
ucuucacgca gaaagcgucu agccauggcg uuaguauag ugucgugcag ccuccaggac       120 cccccucce gggagagcca uaguggucug cggaaccggu gaguacaccg gaauugccag      180
gacgaccggg uccuuucuug gaucaacccg cucaaugccu ggagauuugg gcgugccccc      240
gcgagacugc uagccgagua guguuggguc gcgaaaggcc uugugguacu gccugauagg      300
gugcuugcga gugccccggg aggucucgua gaccgugcac caugagcacg aauccuaaac      360
cucaaagaaa aaccaaaggg cgcgccaugc acccagaaac gcuggugaaa guaaaagaug      420
cugaagauca guugggugca cgagugggguu acaucgaacu ggaucucaac agcgguaaga      480
uccuugagag uuuucgcccc gaagaacguu uuccaaugau gagcacuuuu aaaguucugc      540 uaugugggcgc gguauuaucc cguauugacg ccgggcaaga gcaacucggu cgccgcauac      600
acuauucuca gaaugacuug guugaguacu caccagucac agaaaagcau cuuacggaug      660
gcaugacagu aagagaauua ugcagugcug ccauaaccau gagugauaac acugcggcca      720
acuuacuucu gacaacgauc ggaggaccga aggagcuaac cgcuuuuuug cacaacaugg      780
gggaucaugu aacucgccuu gaucguuggg aaccggagcu gaaugaagcc auaccaaacg      840
acgagcguga caccacgaug ccuguagcaa uggcaacaac guugcgcaaa cuauuaacug      900
gcgaacuacu uacucuagcu ucccggcaac aauuaauaga cuggauggag gcggauaaag      960
uugcaggacc acuucugcgc ucggcccuuc cggcuggcug guuuauugcu gauaaaucug     1020
gagccgguga gcguggggucu cgcgguauca uugcagcacu ggggccagau gguaagcccu     1080
cccguaucgu aguuaucuac acgacgggga gucaggcaac uauggaugaa cgaaauagac     1140
agaucgcuga gauaggugcc ucacugauua agcauuggua aguuaaaaca gaccacaacg     1200
```

-continued

```
guuucccucu agcgggauca auuccgcccc ucucccuccc cccccccuaa cguuacuggc    1260
cgaagccgcu uggaauaagg ccggugugcg uuugucuaua uguuauuuuc caccauauug    1320
ccgucuuuug gcaaugugag ggcccggaaa ccuggcccug ucuucuugac gagcauuccu    1380
aggggucuuu ccccucucgc caaaggaaug caaggucugu ugaaugucgu gaaggaagca    1440
guuccucugg aagcuucuug aagacaaaca acgucuguag cgacccuuug caggcagcgg    1500
aaccccccac cuggcgacag gugccucugc ggccaaaagc cacguguaua agauacaccu    1560
gcaaaggcgg cacaacccca gugccacguu gugaguugga uaguugugga aagagucaaa    1620
uggcucuccu caagcguauu caacaagggg cugaaggaug cccagaaggu accccauugu    1680
augggaucug aucuggggcc ucggugcaca ugcuuuacau uguuuagc gagguuaaaa    1740 aacgucuagg cccccgaac cacggggacg ugguuuuccu uugaaaaaca cgauaauacc    1800
auggaccggg agauggcagc aucgugcgga ggcgcgguuu ucguaggucu gauacucuug    1860
accuugucac cgcacuauaa gcuguccuc gcuaggcuca uaugguugguu acaauauuuu    1920 aucaccaggg ccgaggcaca cuugcaagug uggaucccc cccucaacgu ucgggggggc    1980
cgcgaugccg ucauccuccu cacgugcgcg auccacccag agcuaaucuu uaccaucacc    2040
aaaaucuugc ucgccauacu cggucacuc auggugcucc aggcugguau aaccaaagug    2100
ccguacuucg ugcgcgcaca cgggcucauu cgugcaugca ugcuggugcg gaagguugcu    2160
gggggucauu auguccaaau ggcucucaug aaguuggccg cacugacagg uacgacguu    2220 uaugaccauc ucacccacu gcgggacugg gcccacgcgg gccacgaga ccuugcggug     2280 gcaguugagc ccgucgucuu ucucgauaug gagaccaagg uuaucaccug ggggcagac    2340 accgcgcgu gugggacau caucuuggc cugcccgucu ccgcccgcag ggggagggag     2400
auacaucugg gaccggcaga cagccuugaa gggcaggggu ggcgacuccu cgcgccuauu    2460
acggccuacu cccaacagac gcgaggccua cuuggcugca ucaucacuag ccucacaggc    2520
cgggacagga accaggucga gggggagguc caagugguc ccaccgcaac acaaucuuuc     2580
cuggcgaccu cgucaaugg cgugucuugg acugucuauc auggugccgg cucaaagacc    2640
cuugccggcc caaagggccc aaucacccaa auguacacca auguggacca ggaccucguc    2700
ggcuggcaag cgccccccgg ggcgcguucc uugacaccau gcaccugcgg cagcucggac    2760
cuuuacuugg ucacgaggca ugccgauguc auuccggugc gccggcgggg cgacagcagg    2820
gggagccuac ucuccccag gcccgucucc uacuugaagg gcucuucggg cgguccacug    2880 cucugcccu cggggcacgc ugugggcauc uuucgggcug ccgugugcac ccgagggguu    2940
gcgaaggcgg uggacuuugu acccgucgag ucuauggaaa ccacuaugcg guccccgguc    3000
uucacggaca acucguccc uccggccgua ccgcagacau uccaggu ggc ccaucuacac    3060 gccccuacug guagcggcaa gagcacuaag gugccggcug cguaugcagc caagggguau    3120
aaggugcuug uccugaaccc guccgucgcc gccacccuag guucgggggc guauaugucu    3180
aaggcacaug guaucgaccc uaacaucaga accggggggua ggaccaucac cacgggugcc    3240
cccaucacgu acuccaccua uggcaaguuu cuugccgacg gugguugcuc uggggcgcc    3300 uaugacauca uaauauguga ugagugccac ucaacugacu cgaccacuau ccugggcauc    3360 ggcacaguccu uggaccaagc ggagacgcu ggagcgcgac ucgucgugcu cgccaccgcu    3420 acgcccuccgg gaucgucac cgugcccacau ccaaacaucg aggaggugc ucugccagc     3480 acuggagaaa uccccuuuua uggcaaagcc auccccaucg agaccaucaa ggggggagg    3540
```

```
caccucauuu ucugccauuc caagaagaaa ugugaugagc ucgccgcgaa gcugccggc    3600 cucggacuca augcuguagc auauuaccgg ggccuugaug uauccgucau accaacuagc   3660
ggagacguca uugucguagc aacggacgcu cuaaugacgg gcuuuaccgg cgauuucgac   3720
ucagugaucg acugcaauac augugucacc cagacagucg acuucagccu ggaccccgacc  3780 uucaccauug agacgacgac cgugccacaa gacgcggugu cacgcucgca gcggcgaggc   3840
aggacuggua ggggcaggau gggcauuuac agguuuguga cuccaggaga acggcccucg   3900
ggcauguucg auccucuggu ucugugcgag ugcuaugacg cgggcugugc uugguacgag   3960
cucacgcccg ccgagaccuc aguuagguug cgggcuuacc uaaacacacc aggguugccc   4020
gucugccagg accaucugga guucgggag agcgucuuua caggccucac ccacauagac    4080
gcccauuucu ugucccagac uaagcaggca ggagacaacu uccccuaccu gguagcauac   4140
caggcuacgg ugugcgccag ggcucaggcu ccaccuccau cgugggacca aauguggaag   4200
ugucucauac ggcuaaagcc uacgcugcac gggccaacgc cccugcugua uaggcuggga   4260
gccguucaaa acgagguuac uaccacacac cccauaacca aauacaucau ggcaugcaug   4320
ucggcugacc uggaggucgu cacgagcacc ugggugcugg uaggcggagu ccuagcagcu   4380
cuggccgcgu auugccugac aacaggcagc guggucauug ugggcaggau caucuugucc   4440
ggaaagccgg ccaucauucc cgacagggaa guccuuuacc gggaguucga ugagauggaa   4500
gagugcgccu cacaccuccc uuacaucgaa cagggaaugc agcucgccga acaauucaaa   4560
cagaaggcaa ucgggguugcu gcaaacagcc accaagcaag cggaggcugc ugcucccgug   4620
guggaaucca aguggcggac ccucgaagcc uucugggcga agcauaugug gaauuucauc   4680
agcgggauac aauauuuagc aggcuugucc acucugccug gcaaccccgc gauagcauca   4740
cugauggcau ucacagccuc uaucaccagc ccgcucacca cccaacauac ccuccuguuu   4800
aacauccugg ggggauggu ggccgcccaa cuugcuccuc ccagcgcugc uucugcuuuc    4860
guaggcgccg gcaucgcugg agcggcuguu ggcagcauag gccuugggaa ggugcuugug   4920
gauauuuugg cagguuaugg agcaggggug gcaggcgcgc ucguggccuu uaaggucaug   4980
agcggcgaga ugcccuccac cgaggaccug guuaaccuac cccugcuau ccucucccccu    5040 ggcgcccuag ucgucggggu cgugugcgca gcgauacgc gucggcacgu gggcccaggg   5100 gaggggggcug ugcaguggau gaaccggcug auagcguucg cuucgcgggg uaaccacguc   5160 uccccccacgc acuaugugcc ugagagcgac gcugcagcac gugucacuca gauccucucu  5220
agucuuacca ucacucagcu gcugaagagg cuuccaagu ggaucaacga ggacugcucc    5280
acgccaugcu ccggcucgug gcuaagagau guuugggauu ggauaugcac ggguugacu    5340 gauuucaaga ccuggcucca guccaagcuc cugccgcgau ugccgggagu cccccuucuc   5400
ucaugucaac gugggucaa gggagucugg cgggggcgacg gcaucaugca aaccaccugc   5460
ccauguggag cacagaucac cggacaugug aaaaacgguu ccaugaggau cgugggggccu    5520 aggaccugua guaacacgug gcauggaaca uuccccauua acgcguacac cacgggcccc   5580
ugcacgcccu ccccggcgcc aaauuauucu agggcgcugu ggcgggugge ugcugaggag   5640 uacguggagg uuacgcgggu gggggauuuc acuacguga cgggcaugac cacugacaac   5700
guaaagugcc cgucaggu uccggccccc gaauucuuca cagaaguggga uggggugcgg   5760 uugcacaggu acgcuccagc gugcaaaccc cuccuacggg aggaggucac auuccugguc   5820
gggcucaauc aauaccuggu ugggucacag cucccaugcg agcccgaacc ggacuagca    5880 gugcucacuu ccaugcucac cgaccccucc cacauuacgg cggagacggc uaagcguagg   5940
```

-continued

| | |
|---|---|
| cuggccaggg gaucucccc cuccuuggcc agcucaucag cuauccagcu gucugcgccu | 6000 |
| uccuugaagg caacaugcac uacccgucau gacuccccgg acgcugaccu caucgaggcc | 6060 |
| aaccuccugu ggcggcagga gaugggcggg aacaucaccc gcguggaguc agaaaauaag | 6120 |
| guaguaauuu uggacucuuu cgagccgcuc caagcggagg aggaugagag ggaaguaucc | 6180 |
| guuccggcgg agauccugcg gagguccagg aaauucccuc gagcgaugcc cauaugggca | 6240 |
| cgcccggauu acaaccccucc acuguuagag uccuggaagg acccggacua cgucccucca | 6300 |
| gugguacacg ggguguccauu gccgccugcc aaggcccccuc cgauaccacc uccacggagg | 6360 |
| aagaggacgg uugccugguc agaaucuacc gugucuucug ccuggcgga gcucgccaca | 6420 |
| aagaccuucg gcagcuccga aucgucggcc gucgacagcg gcacggcaac ggccucuccu | 6480 |
| gaccagcccu ccgacgacgg cgacgcggga uccgacguug agucguacuc cuccaugccc | 6540 |
| ccccuugagg gggagccggg ggaucccgau cucagcgacg ggucuugguc uaccguaagc | 6600 |
| gaggaggcua gugaggacgu cgucugcugc ucgaugaccu acacauggac aggcgcccug | 6660 |
| aucacgccau gcgcugcgga ggaaaccaag cugcccauca augcacugag caacucuuug | 6720 |
| cuccgucacc acaacuuggu cuaugcuaca acaucucgca gcgcaagccu gcggcagaag | 6780 |
| aaggucaccu uugacagacu gcagguccug gacgaccacu accgggacgu gcucaaggag | 6840 |
| augaaggcga aggcguccac aguuaaggcu aaacuucuau ccguggagga agccuguaag | 6900 |
| cugacgcccc cacauucggc cagaucuaaa uuuggcuaug gggcaaagga cguccggaac | 6960 |
| cuauccagca aggccguuaa ccacauccgc uccgugugga aggacuugcu ggaagacacu | 7020 |
| gagacaccaa uugacaccac caucauggca aaaaaugagg uuuucugcgu ccaaccagag | 7080 |
| aagggggggcc gcaagccagc ucgccuuauc guauucccag auuugggggu ucgugugugc | 7140 |
| gagaaaaugg cccuuuacga uguggucucc acccucccuc aggccgugau gggcucuuca | 7200 |
| uacgqauucc aauacucucc uggacagcgg gucgaguucc uggugaaugc cuggaaagcg | 7260 |
| aagaaaugcc cuaugggcuu cgcauaugac acccgcuguu uugacucaac ggucacugag | 7320 |
| aaugacaucc uguuuagga gucaaucuac caauguugug acuuggcccc cgaagccaga | 7380 |
| caggccauaa ggucgcucac agagcggcuu uacaucgggg gccccugac uaauucuaaa | 7440 |
| gggcagaacu gcggcuaucg ccggugccgc gcgagcggug uacugacgac cagcugcggu | 7500 |
| aauacccuca cauguuacuu gaaggccgcu gcggccuguc gagcugcgaa gcuccaggac | 7560 |
| ugcacgaugc ucguaugcgg agacgaccuu gucguuaucu gugaaagcgc ggggacccaa | 7620 |
| gaggacgagg cgagccuacg ggccuucacg gaggcuauga cuagauacuc ugccccccu | 7680 |
| ggggacccgc ccaaaccaga auacgacuug gaguugauaa caucaugcuc uccaaugug | 7740 |
| ucagucgcgc acgaugcauc uggcaaaagg guguacuauc ucacccguga ccccaccacc | 7800 |
| cccccuugcgc gggcugcgug ggagacagcu agacacacuc cagucaauuc cuggcuaggc | 7860 |
| aacaucauca uguaugcgcc caccuugugg gcaaggauga uccugaugac ucauuucuuc | 7920 |
| uccauccuuc uagcucagga acaacuugaa aaagcccuag auugucagau cuacggggcc | 7980 |
| uguuacucca uugagccacu ugaccuaccu cagaucauuc aacgacucca uggccuuagc | 8040 |
| gcauuucac uccauaguua cucuccaggu gagaucaaua ggguggcuuc augccucagg | 8100 |
| aaacuugggg uaccgcccuu gcgagucugg agacaucggg ccagaaguqu ccgcgcuagg | 8160 |
| cuacugucc agggggggag ggcugccacu uguggcaagu accucuucaa cugggcagua | 8220 |
| aggaccaagc ucaaacucac uccaauccgg gcugcguccc aguuggauuu auccagcugg | 8280 |

-continued

| | |
|---|---|
| uucguugcug guuacagcgg gggagacaua uaucacagcc ugucucgugc ccgaccccgc | 8340 |
| ugguucaugu ggugccuacu ccuacuuucu guagggguag gcaucuaucu acuccccaau | 8400 |
| cgaugaaggu uggggguaaac acuccggccu cuuaggccau uuccucucuu uuuuuuguuu | 8460 |
| uuuugggguuu uuuuguuuuu uuucuuuuuu uuuuuuuuuu uuucuuuuuu ccuucuuccu | 8520 |
| uuucucuuuu uuucuucuuu aauggugggcu ccaucuuagc ccuagucacg gcuagcugug | 8580 |
| aaagguccgu gagccgcaug acugcagaga gugcugauac uggccucucu gcagaucaug | 8640 |
| uggguucggca uggcaucucc accuccucgc ggccgaccu gggcauccga aggaggacgu | 8700 |
| cguccacucg gauggcuaag ggagagcucu ag | 8732 |

<210> SEQ ID NO 2
<211> LENGTH: 8085
<212> TYPE: DNA
<213> ORGANISM: Artificial Sequence
<220> FEATURE:
<223> OTHER INFORMATION: HCV replicon

<400> SEQUENCE: 2

| | |
|---|---|
| gccagccccc gauugggggc gacacuccac cauagaucac ucccucgugu gaacuaccu | 60 |
| tcttcacgca gaaagcgtct agccatggcg ttagtatgag tgtcgtgcag cctccaggac | 120 |
| cccccctccc gggagagcca tagtggtctg cggaaccggt gagtacaccg gaattgccag | 180 |
| gacgaccggg tcctttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta daccgtgcac catgagcacg aatcctaaac | 360 |
| ctcaaagaaa aaccaaaggg cgcgccatgc acccagaaac gctggtgaaa gtaaaagatg | 420 |
| ctgaagatca gttgggtgca cgagtgggtt acatcgaact ggatctcaac agcggtaaga | 480 |
| tccttgagag tttttcgccc gaagaacgtt ttccaatgat gagcactttt aaagttctgc | 540 |
| tatgtggcgc ggtattatcc cgtattgacg ccgggcaaga gcaactcggt cgccgcatac | 600 |
| actattctca gaatgacttg gttgagtact caccagtcac agaaaagcat cttacggatg | 660 |
| gcatgacagt aagagaatta tgcagtgctg ccataaccat gagtgataac actgcggcca | 720 |
| acttacttct gacaacgatc ggaggaccga aggagctaac cgcttttttg cacaacatgg | 780 |
| gggatcatgt aactcgcctt gatcgttggg aaccggagct gaatgaagcc ataccaaacg | 840 |
| acgagcgtga caccacgatg cctgtagcaa tggcaacaac gttgcgcaaa ctattaactg | 900 |
| gcgaactact tactctagct tcccggcaac aattaataga ctggatggag gcggataaag | 960 |
| ttgcaggacc acttctgcgc tcggcccttc cggctggctg gtttattgct gataaatctg | 1020 |
| gagccggtga gcgtggggtct cgcggtatca ttgcagcact ggggccagat ggtaagccct | 1080 |
| cccgtatcgt agttatctac acgacgggga gtcaggcaac tatggatgaa cgaaatagac | 1140 |
| agatcgctga gataggtgcc tcactgatta agcattggta gtttaaaaca gaccacaacg | 1200 |
| gtttccctct agcgggatca attccgcccc tctccctccc ccccccctaa cgttactggc | 1260 |
| cgaagccgct tggaataagg ccggtgtgcg tttgtctata tgttattttc caccatattg | 1320 |
| ccgtcttttg gcaatgtgag ggcccggaaa cctggccctg tcttcttgac gagcattcct | 1380 |
| aggggtcttt cccctctcgc caaaggaatg caaggtctgt tgaatgtcgt gaaggaagca | 1440 |
| gttcctctgg aagcttcttg aagacaaaca acgtctgtag cgaccctttg caggcagcgg | 1500 |
| aaccccccac ctggcgacag gtgcctctgc ggccaaaagc cacgtgtata agatacacct | 1560 |
| gcaaaggcgg cacaaccccca gtgccacgtt gtgagttgga tagttgtgga aagagtcaaa | 1620 |

-continued

```
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca     1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt tcttgccga cggtggttgc     2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga atcccctttt atggcaaag ccatccccat cgagaccatc      2880
aagggggga ggcacctcat tttctgccat tccaagaaga aatgtgatga gctcgccgcg     2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cggcatgtt cgattcctcg gttctgtgcg agtgctatga cgcgggctgt     3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca aacagaaggc aatcgggttg ctgcaaacag ccaccaagca agcggaggct    3960
```

```
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatgg gtggccgccc aacttgctcc tcccagcgct     4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag ggagggggc tgtgcagtgg atgaaccggc tgatagcgtt cgcttcgcgg      4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740 gtcccctttct tctcatgtca acgtgggtac aaggagtct ggcggggcga cggcatcatg     4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcgg gtggggatt ccactacgt gacgggcatg       5040 accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctgcccag    5340
ctgtctgcgc cttccttgaa ggcaacatgc actacccgtc atgactcccc ggacgctgac    5400
ctcatcgagg ccaacctcct gtggcggcag gagatgggcg gaacatcac ccgcgtggag      5460 tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggaaccg ggggaccccg atctcagtga cgggtcttgg    5940
tctaccgtga gcgaggaagc tagtgaggat gtcgtctgct gctcaatgtc gtatacatgg    6000
acaggcgcct tgatcacgcc atgcgctgcg gaggaaagca agctgcccat caacgcgttg    6060
agcaactctt tgctgcgcca ccataacatg gtttatgcca caacatctcg cagcgcaggc    6120
ctgcggcaga agaaggtcac ctttgacaga ctgcaagtcc tggacgacca ctaccggac     6180 gtgctcaagg agatgaaggc gaaggcgtcc acagttaagg ctaaactcct atccgtagag    6240
gaagcctgca gctgacgcc cccacattcg gccaaatcca agtttggcta tggggcaaag     6300
gacgtccgga acctatccag caaggccgtt aaccacatcc actccgtgtg gaaggacttg    6360
```

```
-continued ctggaagaca ctgtgacacc aattgacacc accatcatgg caaaaaatga ggttttctgt    6420
gtccaaccag agaaaggagg ccgtaagcca gcccgcctta tcgtattccc agatctggga    6480
gtccgtgtat gcgagaagat ggccctctat gatgtggtct ccaccCttcc tcaggtcgtg    6540
atgggctcct catacggatt ccagtactct cctgggcagc gagtcgagtt cctggtgaat    6600
acctggaaat caaagaaaaa ccccatgggc ttttcatatg acactcgctg tttcgactca    6660
acggtcaccg agaacgacat ccgtgttgag gagtcaattt accaatgttg tgacttggcc    6720
cccgaagcca gacaggccat aaaatcgctc acagagcggc tttatatcgg gggtcctctg    6780
actaattcaa aagggcagaa ctgcggttat cgccggtgcc gcgcgagcgg cgtgctgacg    6840
actagctgcg gtaacaccct cacatgttac ttgaaggcct ctgcagcctg tcgagctgcg    6900
aagctccagg actgcacgat gctcgtgaac ggagacgacc ttgtcgttat ctgtgaaagc    6960
gcgggaaccc aagaggacgc ggcgagccta cgagtcttca cggaggctat gactaggtac    7020
tctgcccccc ccggggaccc gccccaacca gaatacgact tggagctgat aacatcatgt    7080
tcctccaatg tgtcggtcgc ccacgatgca tcaggcaaaa gggtgtacta cctcacccgt    7140
gatcccacca ccccctcgc acgggctgcg tgggaaacag ctagacacac tccagttaac    7200
tcctggctag gcaacattat catgtatgcg cccactttgt gggcaaggat gattctgatg    7260
actcacttct tctccatcct tctagcacag gagcaacttg aaaaagccct ggactgccag    7320
atctacgggg cctgttactc cattgagcca cttgacctac ctcagatcat tgaacgactc    7380
catggcctta gcgcattttc actccatagt tactctccag gtgagatcaa tagggtggct    7440
tcatgcctca ggaaacttgg ggtaccgccc ttgcgagctt ggagacaccg ggcccggaat    7500
gtccgcgcta ggcttctgtc cagaggaggc agggctgcca tatgtggcaa gtacctcttc    7560
aactgggcag taaggacaaa gcttaaactc actccaatag cggccgctgg ccggctggac    7620
ttgtccagct ggttcacggc tggctacagc ggggagaca tttatcacgg cgtgtctcat    7680
gcccggcccc gctggttctg gttttgccta ctcctgctcg ctgcaggaat aggcatctac    7740
ctcctcccca atcgatgaag gttggggtaa acactccggc ctcttaggcc atttcctctc    7800
ttttttttgt tttttgggt tttttgttt tttttcttt ttttttttt tttttctttt    7860 ttccttcttc cttttctctt tttttcttct ttaatggtgg ctccatctta gcccctagtca    7920 cggctagctg tgaaaggtcc gtgagccgca tgactgcaga gagtgctgat actggcctct    7980
ctgcagatca tgtgggtcgg catggcatct ccacctcctc gcggtccgac ctgggcatcc    8040
gaaggaggac gtcgtccact cggatggcta agggagagct ctaga                    8085
```